(12) United States Patent
Willis

(10) Patent No.: US 8,227,206 B1
(45) Date of Patent: Jul. 24, 2012

(54) METHOD AND KIT OF DETECTING PREGNANCY

(75) Inventor: Erin Lynn Willis, Lawrence, KS (US)

(73) Assignee: Memphis Zoo, Inc., Memphis, TN (US)

( * ) Notice: Subject to any disclaimer, the term of this patent is extended or adjusted under 35 U.S.C. 154(b) by 0 days.

(21) Appl. No.: 13/429,295

(22) Filed: Mar. 23, 2012

Related U.S. Application Data

(60) Provisional application No. 61/467,146, filed on Mar. 24, 2011.

(51) Int. Cl.
*C12Q 1/26* (2006.01)
*C12N 9/02* (2006.01)
*C07K 1/00* (2006.01)

(52) U.S. Cl. ............................. 435/25; 435/189; 530/350

(58) Field of Classification Search .................... 435/25, 435/189; 530/350
See application file for complete search history.

(56) References Cited

OTHER PUBLICATIONS

Robinson et al., Archives of Biochemistry and Biophysics, 120, 428-433, 1967.*

Willis EL, The acute phase protein ceruloplasmin as a non-invasive marker of pseudopregnancy, pregnancy, and pregnancy loss in the giant panda. PLoS One. 2011;6(7).

Ulutas, P.A. et al., Acute phase protein levels in pregnancy and oestrus cycle in bitches, Res. Vet. Sci. (2008), doi:10.1016/j.rvsc.2008.09.001.

Sunderman FW, Measurement of Human Serum Ceruloplasmin by its p-Phenylenediamine Oxidase Activity, Clinial Chemistry, vol. 16, No. 11, 1970.

* cited by examiner

*Primary Examiner* — Maryam Monshipouri
(74) *Attorney, Agent, or Firm* — Harris Shelton Hanover Walsh, PLLC

(57) ABSTRACT

The present invention disclosed a method to detect pregnancy and identify pseudopregnancy, pregnancy and pregnancy loss using ceruloplasmin as a non-invasive marker in animal urine samples. More specifically, this invention provide provides a method to use a non-invasive marker of inflammation, the acute phase protein ceruloplasmin, in urine samples to detect pregnancy and to distinguish between pregnancy and pseudopregnancy in mammals. The steps of this method include: collecting fresh urine sample from a mammal, adding a ceruloplasmin substrate to the urine sample, measuring oxidase activity of said ceruloplasmin through a sequential reading of absorbance of a photometric product using a spectrophotometer to determine the concentration of ceruloplasmin in the at least one urine sample.

18 Claims, 15 Drawing Sheets

METHOD AND KIT OF DETECTING PREGNANCY

RELATED APPLICATIONS

This application claims the benefit of U.S. Provisional Application Ser. No. 61/467,146 filed Mar. 24, 2011, under 35 U.S.C. Section 1.119(e) hereby specifically incorporated by reference in its entirety.

BACKGROUND OF THE INVENTION

1. Field of the Invention

The present invention relates to a method detecting ceruloplasmin levels in urine samples for pregnancy screening in animals. More particularly, the present invention disclosed a method to identify pseudopregnancy, pregnancy, and pregnancy loss using an acute phase protein ceruloplasmin as a non-invasive marker.

2. Description of the Related Art

Ceruloplasmin (Cp) is a multicopper oxidase enzyme involved in the safe handling of oxygen in some metabolic pathways of vertebrates. Discovered in 1948, a blue protein from the a2-giobulin fraction of human serum possessing oxidase activity towards aromatic diamines and catechol was purified by Holmberg and Laurell (Homberg and Laurell, 1948). It was denoted ceruloplasmin, literally meaning 'a blue substance from plasma'. Specialized copper sites have been recruited during evolution to provide long-range electron transfer reactivity and oxygen binding and activation in proteins destined to cope with oxygen reactivity in different organisms. Ceruloplasmin belongs to the family of multicopper oxidases which are among the few enzymes able to bind molecular oxygen to perform its complete reduction to water (Malmstrom B G, 1982; Farver O. and Pecht I., 1997). Ceruloplasmin contains 95% of the copper in serum (Harris and Gitlin, 1996). Cp found in serum is expressed in the liver, but it is also expressed in the brain, lung, spleen and testis. Aceruloplasminaemia is an autosomal recessive disorder of iron metabolism characterized by the complete absence of ceruloplasmin (Yoshida et al., 1995; Harris et al., 1995). The role of Cp in tissue iron overload and the subsequent clinical findings of diabetes, retinal degeneration and neurodegeneration has been associated with iron overload in aceruloplasminaemic patients (Takahashi et al., 1996). Thus it is clearly indicated that ceruloplasmin plays an essential role in iron metabolism. Evaluation of Ceruloplasmin Activity is commonly used for diagnosis of copper metabolism disorders in humans such as Wilson's disease due to the high affinity of copper for the ceruloplasmin protein (Macintyre et al, 2004; Merle et al., 2009; Sunderman and Nomoto, 1970).

Ceruloplasmin is also associated with reproduction. Copper-deficient female rats seem to be protected against mortality. This protection has been suggested to be provided by estrogens, since estrogens alter the subcellular distribution of copper in the liver, an increase in plasma copper levels and subsequent ceruloplasmin synthesis (Fields et al., 1986). The cause of elevated ceruloplasmin during pregnancy is currently unknown but may related to role of ceruloplasmin in the immunologic recognition of the fetus, inflammatory responses occurring during pregnancy, iron homeostasis, angiogenesis, and/or oxidant defenses. Enzymatic assays for the determination of ceruloplasmin oxidase activity have been described to have greater biological relevance than determination of total ceruloplasmin protein concentration by immulogic techniques that can report ceruloplasmin protein with no enzymatic activity (Macintyre et al, 2004; Merle et at., 2009).

As mentioned previously, ceruloplasmin is the major copper-carrying protein in the blood serum. Its primary clinical function is to detect Wilson's Disease that is an inherited disorder in which there is too much copper in the body's tissues. U.S. Pat. No. 7,407,743 disclosed an assay to measure ceruloplasmin concentration on a blood spot in order to screen Wilson's Disease in population. Although serum levels of some acute phase proteins typically associated with the immune system and inflammation were found to increase during pregnancy in mammals such as humans and dogs (Vannucchi, 2002; Markowitz 1955; Burrows 1971; Ulntas 2009), daily and even weekly blood collections from mammals, especially endangered/exotic species, are challenging to obtain. For example, it is difficult to collect blood samples regularly in giant pandas and polar bears. Therefore, it is necessary to find alternative method to detect pregnancy non-invasively in animal urine samples. In addition, it is also necessary to use urine non-invasive method to distinguish between pregnancy and pseudopregnancy in animals.

SUMMARY OF THE INVENTION

The results described herein present the first physiological test to determine pregnancy status in this species through a non-invasive urinary assay that measures the acute phase protein ceruloplasmin. The present invention disclosed a method and kit to detect pregnancy and identify pseudopregnancy, pregnancy and pregnancy loss using ceruloplasmin as a non-invasive marker in animal urine samples. More specifically, this invention provides a method to use a non-invasive marker of inflammation, the acute phase protein ceruloplasmin, in urine samples to detect pregnancy and to distinguish between pregnancy and pseudopregnancy in animals, particularly in exotic species such as giant panda. The present invention disclosed that the activity of ceruloplasmin increased in urine of pregnant giant pandas compared to non-pregnant animals and that this increase occurs early in gestation allowing for a diagnosis of pregnancy within one week after breeding.

More specifically, this invention provides a pregnancy detecting method of evaluating at least one urine sample for ceruloplasmin from a mammal test subject, such as a giant panda. The steps of this method include: collecting at least one fresh urine sample from a test subject, adding a ceruloplasmin substrate to said at least one urine sample, measuring oxidase activity of the ceruloplasmin through a sequential reading of absorbance of a photometric product using a spectrophotometer to determine the concentration of ceruloplasmin in the at least one urine sample.

More specifically, this invention provides a method for detection of pregnancy of at least one urine sample for ceruloplasmin from a mammalian test subject comprising the steps of: collecting at least one fresh urine sample from a test subject; adding a substrate specific to ceruloplasmin to said at least one urine sample; measuring oxidase activity of said ceruloplasmin through a sequential reading of optical density for oxidase activity of ceruloplasmin; using a ceruloplasmin standard to construct a standard curve of ceruloplasmin; determining the level of ceruloplasmin in said at least one urine sample using the said standard curve; determining the base line level activity of ceruloplasmin using the said enzymatic test kit from a nonpregnant mammal of the same species; and determing an elevated level of said oxidase activity of ceruloplasmin in the test sample greater than that of the baseline level of said oxidase activity of ceruloplasmin from a nonpregnant mammal of the same species, said elevated level of said oxidase activity ceruloplasmin in the test sample being indicative of pregnancy.

More specifically, this invention provides a pregnancy enzymatic test kit for detecting ceruloplasmin level in a test sample of urine from a mammal to determine pregnancy or lack of pregnancy of mammals, said kit comprising: a ceruloplasmin standard to construct a standard curve of ceruloplasmin; assay buffer concentrate, and an substrate specific to ceruloplasmin.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
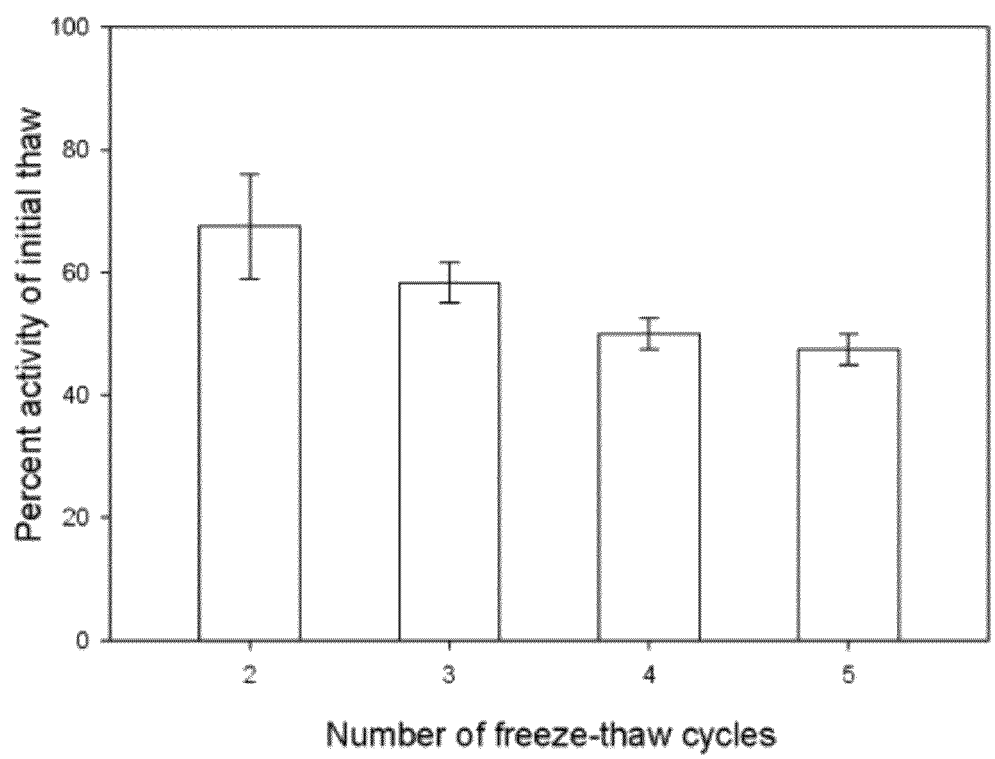
FIG. 1 shows the effect of freeze-thaw cycles on the levels of active ceruloplasmin in urine obtained from giant pandas.

The present invention allows an early detection of pregnancy through quantitative analysis of oxidasic activity of ceruloplasmin in animal urine samples. In one preferred embodiment, the present invention employs non-invasive urine samples that are easy to collect, carry and store in order to avoid using blood serum samples for measuring ceruloplasmin levels. Because the method of the present invention detects and quantifies ceruloplasmin with high sensitivity and accuracy, the method can be used for early pregnancy detection, pseudopregnancy detection and pregnancy loss detection.

Unless defined otherwise, all technical scientific terms used herein have the same meaning as commonly understood herein have the same meaning as commonly understood by one ordinary skilled in the art to which this invention belongs.

In describing the present invention, some terms are defined as follows:

Estrous cycle: The complete reproductive cycle that includes proestrus, estrus, and the luteal phase (the luteal phase encompasses metestrus and diestrus).

Proestrus: The period of time just prior to estrus (sexual receptively), during which a dominant follicle (or follicles) is producing large amounts of estrogens.

Return to baseline progestagen levels or parturition of the luteal phase/pregnancy: The end of the luteal phase, characterized by a decrease in progestagens back to baseline levels in pseudopregnancies or lost pregnancies; or the birth (parturition) of a cub in term pregnancies.

Pseudopregnant cycles: A non-pregnant luteal phase indistinguishable by progestagen levels from pregnant cycles.

Term pregnancy: A pregnancy that is carried the appropriate length until birth.

Primary luteal phase: The period of the luteal phase where progestagens are just slightly above baseline levels.

Secondary luteal phase: The period of the luteal phase where progestagens are substantially above baseline levels.

Secondary rise in progestagens: A marked increase in progestagens above primary luteal phase levels, indicating the end of primary luteal phase and the onset of the secondary luteal phase.

Elevate: A statistically significant increase in the levels of something (for example, a statistically significant increase in the levels active ceruloplasmin in urine).

Inconsistent: A change in the pattern from what is normal. For example, an inconsistency in the pattern of active urinary ceruloplasmin during known and suspected lost pregnancies refers to a different pattern of change over time compared to the normal pattern of change over time found in pregnancies resulting in the birth of a cub.

Deviations: Also refers to a change in the pattern from what is normal. See "inconsistent" above.

The detection of ceruloplasmin can be carried out by measurement of its p-Phenylenediamine (PPD) oxidase activity. The PPD oxidase activity assay for detecting blood serum ceruloplasmin is well-known in the art and can be employed in the present invention for detecting urinary ceruloplasmin levels. The following text is incorporated by reference: Measurement of human serum ceruloplasmin by its p-Phenylenediamine oxidase activity, Clinical Chemistry, Vol 16, No. 11, 1970, F. William Sunderman, Jr. and Shozo Nomoto.

In one preferred embodiment, the quantification of ceruloplasmin is determined by the rate of formation of a colored product from ceruloplasmin and the substrate, N,N-dimethyl-p-phenylendiamine. The rate of colorometric change is proportional to the amount of ceruloplasmin in each sample.

Urine samples from a Giant Panda have been examined for ceruloplasmin (CP) activity for use as a biomarker of pregnancy. Values ranged from those below detection (<0.857 units/mL, or approximately 1 unit/mg creatinine) to >120 units/mg creatinine with the highest values occurring during pregnancy. Urinary CP activity has also been detected in Polar Bears, Sloth Bears, and Spectacled Bears. Further examination of the variation of urinary CP values during the reproductive cycle in these species is ongoing.

The present invention is carried out in urine samples of mammalian test subjects. The urine samples can be fresh or frozen stored. In one embodiment, fresh urine samples from estrous cycles are collected via aspiration from the animal's enclosure and then stored frozen. Three to seven samples per week were analyzed for the weeks of proestrus (when available), estrus, and weeks 1 through the week of baseline progestagen levels or parturition of the luteal phase/pregnancy. Known pseudopregnant cycles when no breeding occurred were used as controls from each female.

Prior to being assayed for ceruloplasmin, urine samples can be centrifuged. In one preferred embodiment, the urine samples are centrifuged at 3500 RPM for 10 minutes and concentrated to 300 µl. Samples were then assayed for ceruloplasmin through oxidasic activity measurement.

After adding the ceruloplasmin substrate to the urine samples for measuring the oxidase activity of ceruloplasmin, the absorbance of the photometric product are measured by a spectrophotometer at wavelength range 550-560 nm. In a preferred embodiment, the change in absorbance of the photometric product was measured sequentially at every 30 seconds for a 5 minute interval using a Biomate 3 UV-Vis spectrophotometer (Thermo Scientific, Waltham, Mass.). The change in absorbance was also measured in a blank control for each run and this value was subtracted from the change in absorbance in each urine sample. Units of ceruloplasmin were calculated based on the difference in the change of absorbance in each sample from the control multiplied by reaction volume per the unit definition of change in absorbance at 550 nm (0.01), volume of enzyme used and the published conversion factor for the unit definition of a 7 ml reaction volume (Curzon and valet, 1960). The inter-assay coefficient of variance was 14.9%. Creatinine was also measured in each urine sample to account for the concentration of water (Monfort et al., 1989; Taussky, 1954), and final ceruloplasmin concentration was expressed per mg of creatinine.

Figure 2:
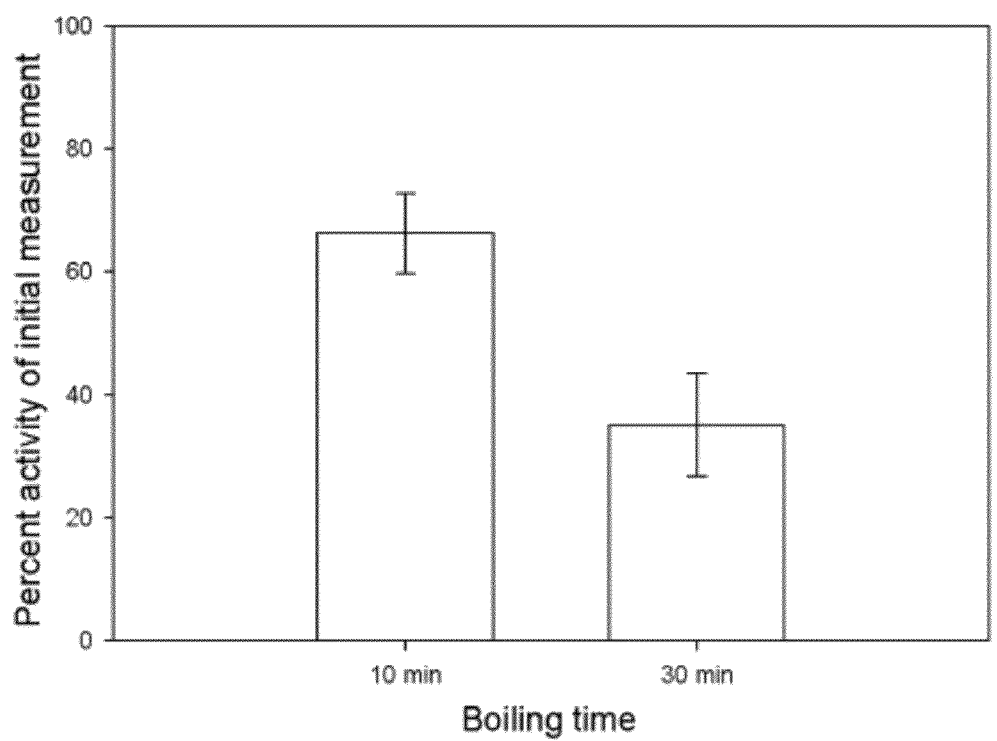
FIG. 2 shows the effects of boiling on the levels of active ceruloplasmin in urine obtained from giant pandas.

The present invention also discloses a validation method for detecting the effects of freeze-thaw cycles and boiling on the level of active ceruloplasmin. Ceruloplasmin assay validations are shown in FIGS. 1-2 and Table 1. In a preferred embodiment, FIG. 1 illustrates the effect of freeze-thaw cycles on the levels of active ceruloplasmin in urine obtained from giant pandas. Repeated freeze-thaw cycles could affect the levels of active ceruloplasmin in urine. Ceruloplasmin activity was decreased by an average of 33, 42, 50, and 53% in the $2^{nd}$, $3^{rd}$, $4^{th}$, and $5^{th}$ thaws, respectively, compared to the activity observed at the initial measurement (set to 100%). Because banked samples had been frozen and thawed on numerous occasions and the exact number of freeze-thaw cycles was unknown and inconsistent between cycles, samples were not analyzed between different cycles. Data are the percent mean decrease in ceruloplasmin activity from the activity found at the initial thaw for the current study ±SEM.; n=3 samples.

In another preferred embodiment, FIG. 2 illustrates the effects of boiling on the levels of active ceruloplasmin in urine obtained from giant pandas. Change in absorbance in each urine sample was measured prior to boiling and then after boiling for 1.0 or 30 minutes. Boiling for 10 minutes produced a decrease in activity by an average of 34%, while boiling for 30 minutes produced a decrease in activity by an average of 65%, compared to the ceruloplasmin activity observed with no treatment (set to 100%). Data are the percent mean decrease in ceruloplasmin activity from the activity found at the initial measurement ±SEM; n=4 samples.

In another preferred embodiment, Table 1 shows comparison of active ceruloplasmin values in sample pools of giant panda urine obtained from the change in absorbance/ml enzyme method and standard curve method. To check the validity that the rate of colorimetric change is proportional to the amount of ceruloplasmin in giant panda urine, values obtained from the change in absorbance/ml enzyme calculation method were compared to values obtained from a standard curve method. For the change in absorbance/ml enzyme calculation method, units of ceruloplasmin in two pools (a high and low pool) were calculated based on the difference in the change of absorbance in each sample from the blank control multiplied by reaction volume per unit definition for the change in absorbance at 550 nm (0.01), volume of enzyme used and the published conversion factor for the unit definition of a 7 ml reaction volume. For the standard curve method, after subtracting the change of absorbance in each sample from the blank control, units of ceruloplasmin in each pool were calculated both manually using the linear regression (LR) equation obtained from the standard curve; y=0.0067x−0.0011 and by using Sigma Plot software (Systat Software Inc., San Jose, Calif.) to calculate the values using a 4-parameter logistic (4PL) curve fit. A. The raw values of active ceruloplasmin for pool dilutions; values are expressed as u/ml enzyme (change in absorbance/ml enzyme method) or u/ml* (standard curve method). B. Raw values of active ceruloplasmin by dilution factor; values are expressed as u/ml enzyme (change in absorbance/ml enzyme method) or u/ ml* (standard curve method). Values are not expressed on a per mg of creatinine basis.

TABLE 1

| | | A. Raw Values | | | B. By Dilution Factor | | |
| --- | --- | --- | --- | --- | --- | --- | --- |
| | Dilution | ml Enzyme u/ml enzyme* | Std Curve-LR u/ml* | Std Curve-4PL u/ml* | ml Enzyme u/ml enzyme* | Std Curve-LR u/ml* | Std Curve-4PL u/ml* |
| Pool 1 (low) | Neat | 1.68 | 1.36 | 1.44 | 1.68 | 1.36 | 1.44 |
| | 1:2 | 1.05 | 0.91 | 0.96 | 2.10 | 1.82 | 1.93 |
| | 1:4 | 0.63 | 0.61 | 0.63 | 2.52 | 2.45 | 2.52 |
| | 1:8 | 0.21 | 0.31 | 0.27 | 1.68 | 2.51 | 2.13 |
| Pool 2 (high) | Neat | 8.19 | 5.99 | 5.94 | 8.19 | 5.99 | 5.94 |
| | 1:2 | 5.25 | 3.90 | 3.93 | 10.50 | 7.79 | 7.87 |
| | 1:4 | 3.57 | 2.70 | 2.78 | 14.28 | 10.81 | 11.12 |
| | 1:8 | 2.10 | 1.66 | 1.74 | 16.80 | 13.25 | 13.96 |

The amount of progestagen in urine samples can be carried out by an enzyme immunoassay utilizing the binding reaction between an antibody and progestagen. Various immunoassays are well-known in the field and any of them can be employed. In a preferred embodiment, an enzyme immunoassay (EIA) using the progestagen antibody (CL425; C. Munro, UC Davis, Calif.) and conjugate (horseradish peroxidase progesterone conjugate; C. Munro, UC Davis, Calif.) was utilized to determine urinary progestagen concentrations. In another preferred embodiment, urinary progestagen concentrations may be measured using a single antibody EIA for the progesterone metabolite, pregnanediol-3-glucuronide (PdG; P-26; C. Munro, UC Davis, Calif.). Both the group-specific CL425 progestagen antibody and the PdG specific antibody are widely used for captive management of the giant panda and a similar relationship was observed between active ceruloplasmin and the secondary rise of progestagens in urine for term pregnant cycles when concentrations of progestageus were analyzed using either antibody.

The present invention also provides a method to verify an animal urine protein similar in molecular weight to human ceruloplasmin urine by mass spectrometry. In a preferred embodiment, Matrix Assisted Laser Desorption/Ionization (MALDI) mass spectrometry was performed at Mississippi State University. Giant panda urine from 3 samples with high ceruloplasmin activity, one sample with extremely low ceruloplasmin activity (negative control) and a purified human ceruloplasmin control (Sigma-Aldrich, St. Louis, Mo.) were prepared using the dried-droplet method, as previously described. MADLI analysis was performed using a Bruker Microflex MALDI time of flight mass spectrometer (Bruker Daltonic, Billerica, Mass.). Only the high mass region was scanned and once a peak was indentified for the human ceruloplasmin control, peaks with similar molecular weights were focused on in the urine samples, and their mass to charge (m/z) values were determined. A protein with similar characteristics and molecular weight to human ceruloplasmin was verified in giant panda urine known to have high levels of ceruloplasmin activity; a peak was observed at 138930.55 m/z, corresponding to ~139 kDa in giant panda urine compared to a peak at 134920.11 m/z, corresponding to a molecular weight ~135 kDa in the human ceruloplasmin control. Ceruloplasmin heterogeneity has previously been found between species (as well as within species due to multiple splice variants, etc.). No defined peaks within this mass range and a very large signal to noise ratio were observed in the negative control urine sample.

The ceruloplasmin oxidase values are analyzed by statistical analysis. In one preferred embodiment, data sets for ceruloplasmin were tested for homogeneity of variance by Hartley's test (Hartley 1950, Neter 1985) and values were log transformed before statistical analysis, if heterogeneous variance was indicated. Changes in weekly ceruloplasmin levels for each cycle were analyzed using a one-way analysis of variance (ANOVA) using JMP 7 Statistical Discovery (SAS, Cary, N.C.). Dunnett's test was used to determine significant differences between weekly means of the luteal phase and that of estrus/proestrus (baseline control) level means. Means were considered different at $P \leqq 0.05$. Graphed ceruloplasmin values are presented as weekly means ±SEM of non-transformed values and represent 3-7 urine samples/week.

For each luteal phase, the primary and secondary rise in urinary progestagens were determined by an iterative method as described previously for fecal progestagens (Kersey 2010). The following text is incorporated by reference: Unique biphasic progestagen profile in parturient and non-parturient giant pandas as determined by faecal hormone monitoring.

Briefly, the primary rise was regarded as the time from the beginning of the luteal phase until the elevation of progestagens to 2 standard deviations above the mean for two or more days, while the secondary rise in urinary progestagens was the duration from the end of the primary rise until the end of the luteal phase. Termination of the luteal phase was defined as either parturition (term pregnancies) or the return to baseline progestagens (all other cycles).

EXAMPLE 1

For decades, researchers all over the world have been searching for a reliable pregnancy test for giant pandas and other exotic wildlife. For example, while over 300 pandas in captivity around the world, but as with any small population, careful management is required to maintain genetic diversity and to prevent inbreeding (IUCN/SSC, 2010). Although significant progress has been made in growing the captive population, giant pandas remain a challenge to breed in captivity due to the single estrous period per year lasting only one to three days, mate incompatibility, lack of sexual interest, and failure to give birth following optimal timing of insemination. Female giant pandas spontaneously ovulate (Chaudhuri et al., 1988), and undergo a phenomenon known as pseudopregnancy if not pregnant, wherein a female's reproductive hormones are similar in concentration and length during the non-pregnant luteal phase as during pregnancy. This makes pregnancy determination impossible by diagnostic hormonal tests typically used in other mammals (Chaudhuri et al., 1988; Monfort, et al., 1989).

In many other species, pregnancy can be diagnosed from hormonal monitoring of the luteal steroid, progesterone, or its excreted metabolites in urine and feces. However, progestagen patterns in pregnant and pseudopregnant pandas are indistinguishable (Chaudhuri et al., 1988; Monfort, et al., 1989; Steinman et al., 2006; Kersey et al., 2010; Kersey et al., 2010). Furthermore, these luteal phases are unpredictable in length. They consist of a variable primary phase lasting anywhere from around 60 to 122 days, which is characterized by a slight increase in progestagens above baseline levels (Steinman et al., 2006; Kersey et al., 2010). The primary rise of progestagens is then followed by a more consistent secondary phase which comprises a substantial increase in progestagens above baseline lasting 40-50 days (Steinman et al., 2006; Kersey et at., 2010). In a pregnant giant panda, the embryo remains quiescent in embryonic diapause until the secondary rise of progestagens when implantation is suspected to occur and the fetus begins to grow rapidly (Chaudhuri et al., 1988; Monfort, et al., 1989; Zhang et al., 2009; Shtherland-Smith et al., 2004; Hodges et al., 1984).

Pregnant females do not show marked changes in behaviors until the last two weeks of gestation, but these behaviors are often inconsistent among females and pseudopregnant females may also exhibit similar changes in behavior prior to the end of the luteal phase (Steinman et al., 2006). In a limited number of cases, ultrasonography has been helpful in the detection of a fetus or gestational sac but is only applicable when used late in pregnancy at about 2 to 3 weeks prior to parturition, following the delayed implantation (Zhang et al., 2009; Shtuerland-Smith et al., 2004). Even then, detection can be challenging and requires the skill of an expert ultrasonographer as well as the cooperation of the animal. While ultrasonography has provided some evidence of failed pregnancies due to embryonic loss in giant pandas (Steinman et al., 2006; Sutherland-Smith et al., 2004; Hildebrandt et al., 2006), if no indications of pregnancy are observed by ultrasound and a cub is not born after progestagens return to baseline, it is usually assumed the female was not pregnant. However, because ultrasound can only detect a fetus in late gestation and females are often uncooperative at this time, many lost pregnancies could very easily go undetected. During one term pregnancy, thermal imaging also showed promise for detecting growing fetal tissue and determining litter size in giant pandas at an earlier stage than ultrasound (durrant et al., 2006). However, this technique still does not differentiate pseudopregnancy from pregnancy until after the time of implantation. For decades, researchers all over the world have been searching for a 'magic bullet' that would provide a pregnancy test for giant pandas and other exotic wildlife that undergo pseudopregnancy. To date, all tests utilizing steroid hormones and their metabolites, as well as other hormones such as relaxin, have proven ineffective for distinguishing between pregnancy and pseudopregnancy (Chaudhuri. et al., 1988; Monfort et al., 1989; Kersey et al., 2010; and Steinetz et al., 2005). Thus, the lack of a reliable pregnancy test continues to limit our ability to understand aspects of conception, delayed implantation/embryonic diapause, embryonic loss and pregnancy maintenance for these species.

Ex-situ conservation of the giant panda began in the 1960s. Due to problems like the lack of breeding in adults and high infant mortality, the giant panda's captive propagation history has been plagued by inconsistent reproductive success. In recent years, considerable improvement has been made in captive reproduction and cub survival due to the application of techniques like artificial insemination and improvement in husbandry and cub rearing (Ellis 2006). The ex-situ population provides numerous benefits to the conservation of this species as a whole (IUCN/SSC 2010). Opportunities for the advancement of basic science in understanding bear biology, a source of captive broodstock for reintroductions and translocations, and an assurance colony against wild population declines are a few of the reasons established by the International Union for the Conservation of Nature for maintaining a captive population (IUCN/SSC 2010). After decades of research on the species' biology and ecology there still remain many unanswered questions, including those related to their reproductive strategy. Pseudopregnancy, delayed implantation/embryonic diapause, and the variable length of the luteal phase in both the pregnant and non-pregnant states are just some of the challenges that complicate research into the reproductive physiology of the giant panda. An accurate and straightforward pregnancy test for giant pandas has eluded scientists for decades, but the ability to distinguish between pregnancy and pseudopregnancy is indispensable for our basic understanding of this species' reproductive biology. Ceruloplasmin is part of a family of acute phase proteins that usually plays a protective role in response to an immune-provoking stimulus. It is a multifunctional copper containing protein that was first isolated in blood in 1948. Thus, it is an important copper transport molecule, but one of its main additional roles is as an antioxidant, as it has substantial ferroxidase activity and can sequester other free radicals. Serum levels of ceruloplasmin have been found to increase during normal pregnancy in some species and it is thought that this increase during gestation protects against oxidative stress associated with pregnancy. In dogs, the increase in serum ceruloplasmin has been coupled to the time of embryonic endometrial implantation and placentation.

Urine from reproductive cycles of the four adult female giant pandas held at North American institutions was used for the study. Females SB507, SB437, SB452 and SB371 were housed at the Memphis Zoological Society (MZS), the Smithsonian National Zoological Park (SNZP), Zoo Atlanta (ZA) and the San Diego Zoo (SDZ), respectively. All animals were fed a diet consisting of at least 85-95% bamboo, with fruit and high fiber biscuits given as treats, and water was provided ad libitum. Urine samples were collected fresh, in a similar manner from each institution, via aspiration from the animal's enclosure and then stored frozen at −20° C. Subsamples of urine (500 ul aliquots) from SNZP, ZA and SDZ were shipped frozen overnight to the MZS for ceruloplasmin analysis. Urine from five adult female polar bears in North American institutions was used for the polar bear preliminary study. Females Haley and Cranbeary were housed at the MZS, Aurora and Nikita were housed at the Toronto Zoo and Chinook was housed at the SDZ. All animals were fed a diet of carnivore diet and fish, along with root vegetables and lettuce, and water was provided ad libitum. Urine samples were collected and shipped to the MZS in a manner similar to the samples obtained from giant pandas.

An enzyme immunoassay (EIA) using the same progestagen antibody (CL425; C. Munro, UCDavis, Calif.) and conjugate (horseradish peroxidase progesterone conjugate; C. Munro, UCDavis, Calif.) was utilized to determine urinary progestagen concentrations for animals from SNZP, ZA and MZS. However, different institutions performed the hormone analyses. For SB437 (SNZP) and SB452 (ZA), urinary progestagens were measured at the SNZP as previously described (Zhang 2009; Sutheland-Smith 2004; Hodges 1984). The concentration of progestagens in urine for SB507 (MZS) was measured at the MZS by a similar single antibody EIA. Urinary progestagens were measured using the broad scale (Hodges 1984) progesterone antibody (CL425) and horseradish peroxidase progesterone conjugate provided by C. Munro (UCDavis, Calif.) and a commercially available progesterone was used for standards (4-Pregnene-3,20-diene; Sigma-Aldrich, St. Louis, Mo.). The antibody was used at a final dilution of 1:6,000 and the sensitivity of the assay was 0.01 ng/ml. Samples were diluted in 0.1 M phosphate buffered saline (19.5% 0.2 M monobasic sodium phosphate, 30.5% 0.2 M dibasic sodium phosphate, 8.7% NaCl, and 1% bovine serum albumin; Sigma-Aldrich, St. Louis, Mo.) prior to being assayed. Standards, samples, and controls were added (50 µl/well) to antibody-coated microtiter plates. Progesterone conjugate at a final dilution of 1:60,000 was added to each well (50 µl/well) and incubated for two hours. After incubation, unbound hormone was removed and the substrate solution (10% 2,2'-Azino-bis(3-ethylbenzothiazoline-6-sulfonic acid) diammonium salt and 3.2% hydrogen peroxide in 9.6% citric acid; Sigma-Aldrich, St. Louis, Mo.) was added (100 µl/well) and allowed to develop in the dark until optical density had reached 1 in the maximum binding wells (~45-60 minutes). Optical densities were read with a Dynex Technologies MRX microtiter plate reader (Thermo Labsystems, Chantilly, Va.). The intra- and inter-assay coefficients of variance were 3.0% and 10.2% and 5.4% and 14.5%, respectively for the low and high controls. Creatinine was measured in each urine sample to account for the concentration of water, and progestagen concentration was expressed as mg of creatinine. Because an accurate assay for progestagen measurement is still being investigated in polar bears, progestagens are not routinely measured in polar bears. However, ovulation and the luteal phase can generally be determined by an absence of repeated estrus behavior after breeding. Unlike giant pandas (who only experience one estrus event per year), polar bears will show repeated estrus behaviors throughout their breeding season (early winter/spring) unless ovulation has occurred after breeding resulting in either a pseudopregnant or pregnant luteal phase.

Urinary progestagen concentrations for SB371 (SDZ) were measured at SDZ using a single antibody EIA for the progesterone metabolite, pregnanediol-3-glucuronide, as previously described. The following text is incorporated by reference: Steinetz B G et. al, 2005, Relaxin concentrations in serum and urine of endangered species: correlations with physiologic events and use as a marker of pregnancy. Ann NY Acad Sci 1041: 367-378). In this assay, PdG antiserum (P-26; C. Munro, UCDavis, Calif.) is combined with horseradish peroxidase PdG conjugate (C. Munro, UCDavis, Calif.). Both the group-specific CL425 progestagen antibody and the PdG specific antibody are widely used for captive management of the giant panda and a similar relationship was observed between active ceruloplasmin and the secondary rise of progestagens in urine for term pregnant cycles when concentrations of progestagens were analyzed using either antibody.

Figure 3:
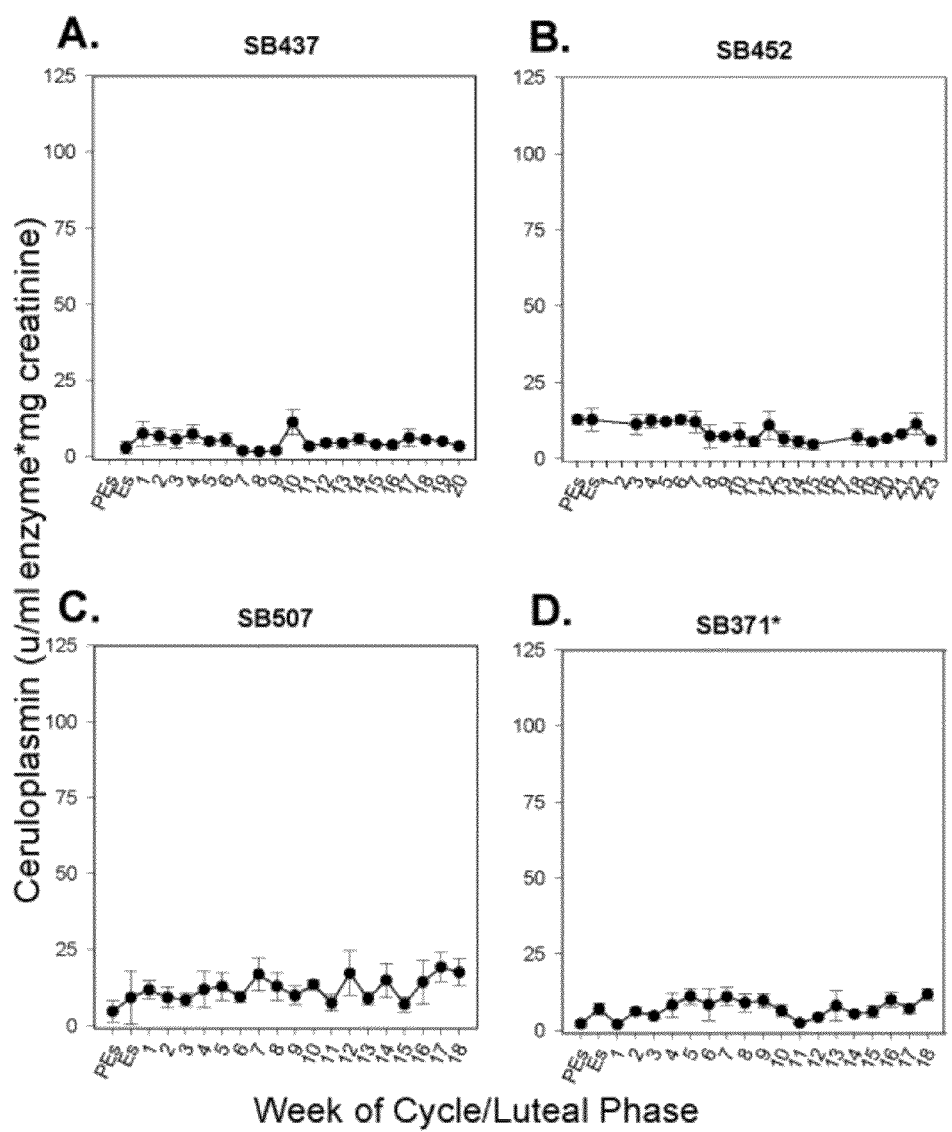
FIG. 3A-3D show the levels of active ceruloplasmin in urine for female giant pandas during known pseudopregnant cycles when no breeding occurred.

Now referring to FIG. 3, no change in the levels of active urinary ceruloplasmin was observed throughout the estrous cycle in known pseudopregnant giant pandas that were not bred. In FIG. 3, the levels of active ceruloplasmin in urine for female giant pandas during known pseudopregnant cycles when no breeding occurred. One known pseudopregnancy when no breeding or AI occurred is depicted for each female giant panda housed in U.S. institutions. Panel A: Known pseudopregnancy in 2002 for SB437 (SNZP). Panel B: Known pseudopregnancy in 2003 for SB452 (ZA). Panel C: Known pseudopregnancy in 2005 for SB507 (MZS). Panel D: Known pseudopregnancy in 1997 for SB371 (SDZ). Urinary progestagens were monitored in each cycle to ensure a normal luteal phase. Urine samples from every week of the reproductive cycle could not be obtained for SB452 during her known pseudopregnancy in 2003. PEs=Proestrus; Es=Estrus; Numerical numbers=weeks of the luteal phase. Variations in the x axis exist to accommodate variable concentrations and durations. Data are weekly means ±SEM; n=4 reproductive cycles. Samples from cycles obtained from SB371 were analyzed blind, without prior knowledge of cycle outcome.

Figure 4:
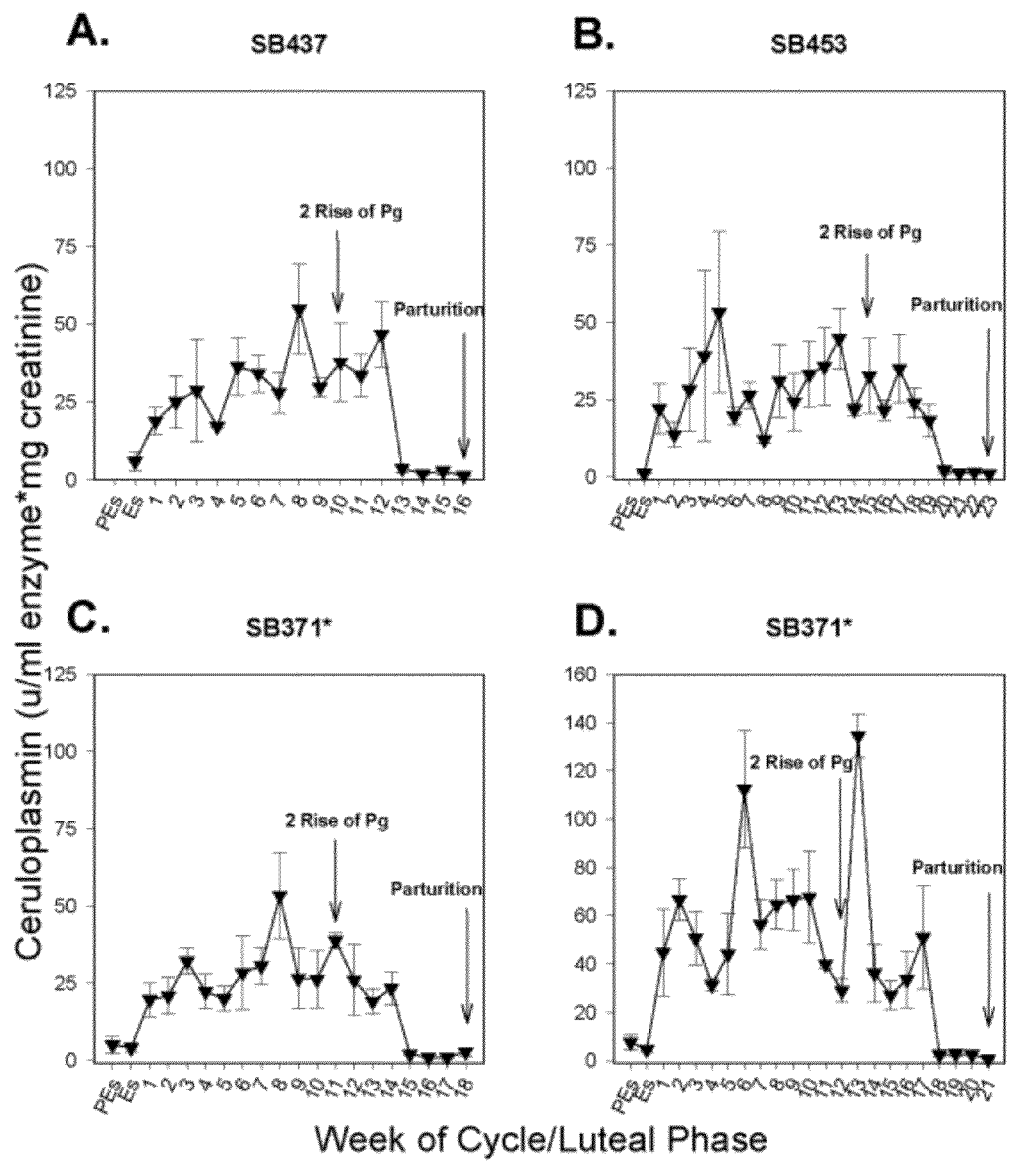
FIG. 4A-4D show the levels of active ceruloplasmin in urine for female giant pandas during representative term pregnant cycles.

However, in pregnancies carried to term, the levels of active ceruloplasmin in urine were elevated by 3.2- to 19.8-fold at week one of the luteal phase compared to the levels observed at proestrus/estrus ($P \leq 0.05$; FIG. 4). These levels then remained high, ranging from 2.8- to 17.5-fold above proestrus/estrus levels, until 20-24 days prior to birth ($P \leq 0.05$; FIG. 4). The secondary rise in progestagens was calculated for each luteal phase in cycles where breeding or artificial insemination (AI) occurred to determine the relationship between the pattern of ceruloplasmin and progestagens.

FIG. 4 illustrates the levels of active ceruloplasmin in urine for female giant pandas during representative term pregnant cycles. Panel A: Term pregnancy in 2005 for SB437 (SNZP). Panel B: Term pregnancy in 2006 for SB452 (ZA). Panel C: Term pregnancy in 1999 for SB371 (SDZ). Panel. D: Term pregnancy in 2003 for SB371 (SDZ). Animals were artificially inseminated (SB437; SB452) or artificially inseminated (SB371, reproductive cycle 1999) and bred naturally (SB371, reproductive cycle 2003). The amount of time active ceruloplasmin levels remained elevated in urine was dependent upon the gestation length of each term pregnancy, but levels consistently remained high through approximately half of the secondary rise in progestagens and then decreased to at or below proestrus/estrus levels 20-24 days prior to parturition in each pregnancy examined. SB371 was confirmed pregnant with twins by ultrasound in 2003, but only gave birth to one cub. All other term pregnant cycles characterized produced a singleton cub. Pg=Progestagen; PEs=Proestrus; Es=Estrus; Numerical numbers=weeks of the luteal phase. Variations in the x and y axes exist to accommodate variable concentrations and durations. Data are weekly means ±SEM; n=5 reproductive cycles, representative cycles (n=4) are presented herein. Samples from SB371 were analyzed blind, without prior knowledge of cycle outcome.

Figure 5:
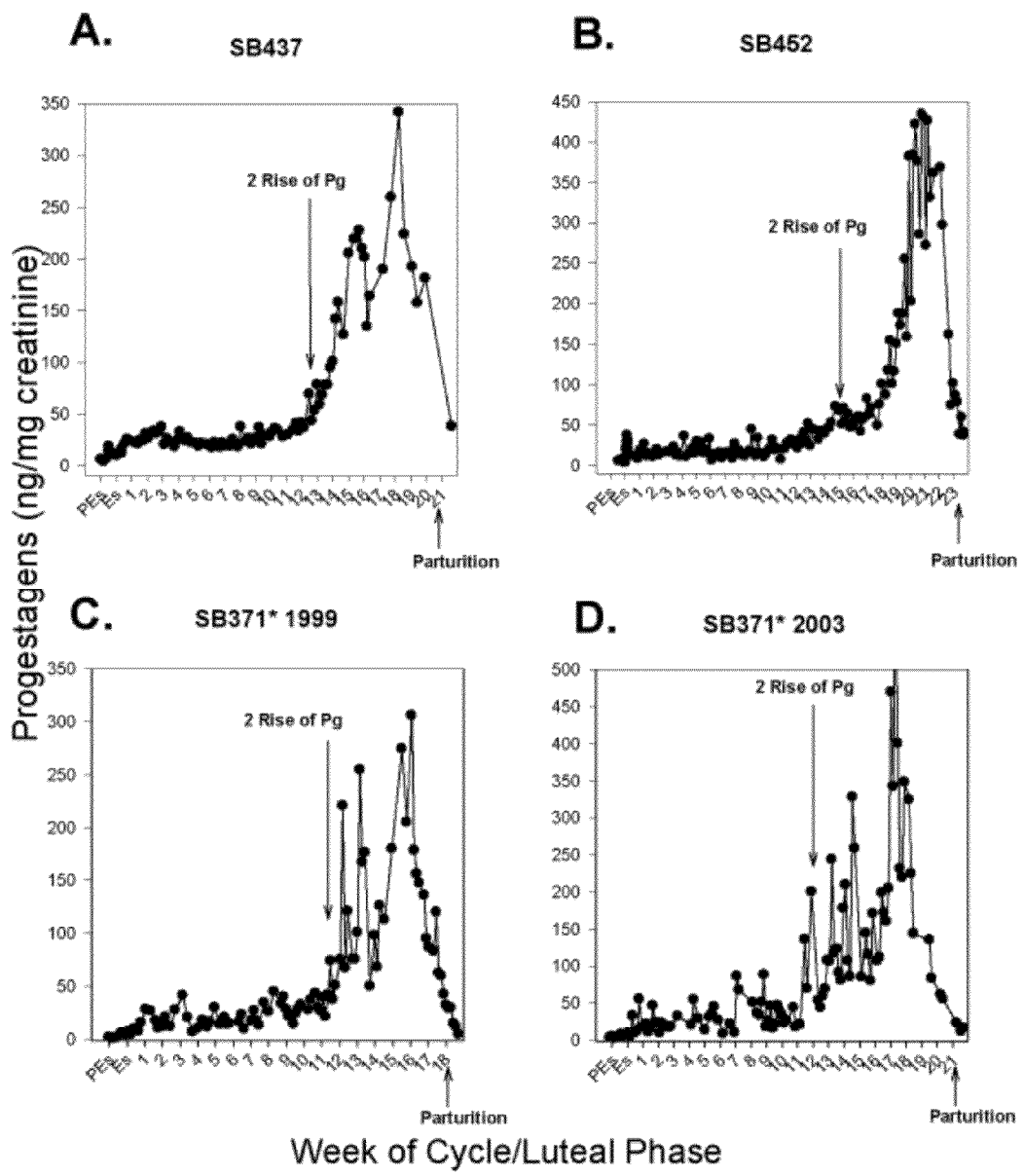
FIG. 5A-5D show urinary progestagens in representative pregnancies carried to term in female giant pandas.

In term pregnancies, ceruloplasmin remained increased for approximately half of the secondary rise in progestagens (ranging from 42-71% of the secondary progestagen rise; FIG. 5) and then declined late in the luteal phase to at or below proestrus/estrus levels for the remainder of the cycle. Cycles obtained from SB371 (San Diego Zoo; SDZ) were analyzed without prior knowledge of cycle outcome. The CEP assay accurately determined the known pseudopregnancy cycle and both term pregnancy cycles from SB371 included in this study. FIG. 5 illustrates urinary progestagens in representative pregnancies carried to term in female giant pandas. Black circles represent urinary progestagen concentrations; Pg=Progestagen; PEs=Proestrus; Es=Estrus; Numerical numbers=weeks of the luteal phase. Variations in the x and y axes exist to accommodate variable concentrations and durations. *Because urinary progestagen concentrations for SB371 were analyzed using a different antibody, caution must be taken when directly comparing progestagen data between SB371 and the other animals. However, the same trends were observed in the relationship between active ceruloplasmin and progestagens in urine using both antibodies.

Indications of pregnancy after AI were observed by ultrasound in animal SB507 (Memphis Zoological Society, MZS) in 2007 and 2010 but no birth occurred in either year. In 2007, a gestational sac was observed two weeks prior to the end of the luteal phase, or baseline progestagens. No further development was observed and the gestational sac degraded and regressed in the following weeks. In 2010, an early-stage fetus with a heartbeat was observed in the left uterine horn three weeks prior to baseline progestagens. However, no growth or heartbeat was observed the following week. The gestational sac then continued to degrade and regress in the weeks thereafter. In these confirmed lost pregnancies, the levels of active urinary ceruloplasmin were elevated during the luteal phase but the pattern was inconsistent with levels observed for term pregnancies (FIGS. 6A and B). For the luteal phase in 2007, levels of active ceruloplasmin did not increase until week 5 and a consistent increase above proestrus/estrus levels did not occur until week 7 ($P \leq 0.05$; FIG. 6A). Interestingly, during the late luteal phase the levels of active urinary ceruloplasmin failed to remain at proestrus/estrus baseline values as was observed in pregnancies carried to term. After the initial decline during the late luteal phase, active ceruloplasmin increased again above baseline at week 18 ($P \leq 0.05$; FIG. 6A). Active urinary ceruloplasmin increased by 5.4-fold above proestrus/estrus levels during the first week of the 2010 luteal phase, similar to what was observed in term pregnancies ($P \leq 0.05$). However, marked inconsistencies compared to term pregnancies were observed during the late luteal phase (FIG. 6B). For example, the decline in ceruloplasmin during the end of the cycle occurred early in relation to the secondary rise in progestagens with ceruloplasmin decreasing just six days after the secondary rise (FIG. 6D). Thus, the levels of active ceruloplasmin remained elevated for only 14% of the secondary rise in progestagens compared to 42-71% in term pregnancies. In addition, although the levels of active urinary ceruloplasmin decreased to estrus/proestrus levels at week 12, they did not remain consistently low and increased above control levels at week 16 ($P \leq 0.05$), similar to the abnormal pattern observed during the late luteal phase of SB507's lost pregnancy in 2007 (FIG. 6A).

Figure 6:
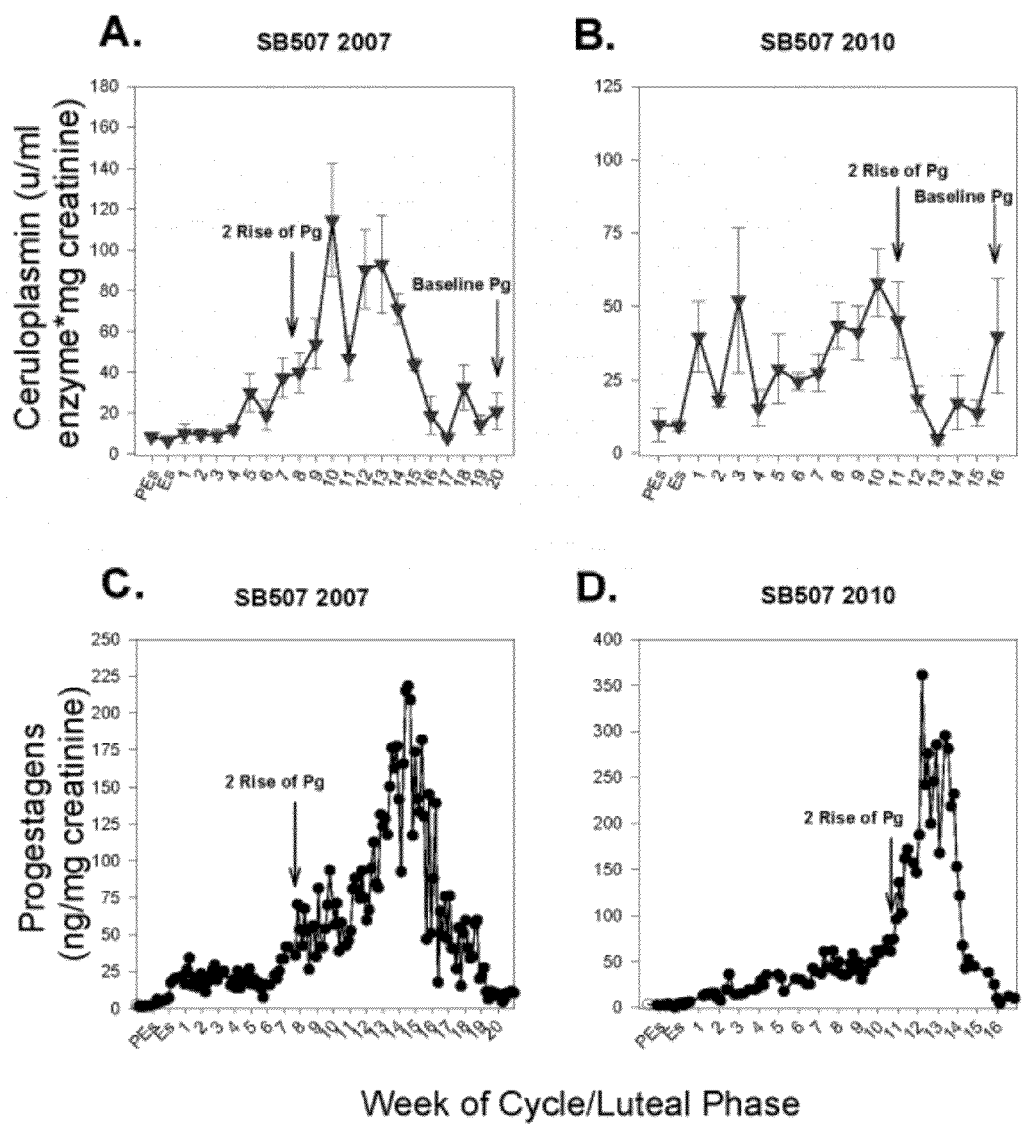
FIG. 6A-6D show the levels of active urinary ceruloplasmin and urinary progestagens in lost pregnancies for female SB507.

FIG. 6 illustrates the levels of active urinary ceruloplasmin and urinary progestagens in lost pregnancies for female SB507. SB507 (MZS) was confirmed pregnant after artificial insemination in 2007 and 2010 by ultrasound at weeks 18 and 13, respectively; however, retarded growth was observed by ultrasound in the weeks thereafter and no birth occurred in either year. The levels of active urinary ceruloplasmin in 2007 (6A) and 2010 (6B) for SB507. Panels 6C and: D: The levels of urinary progestagens in 2007 (6C) and 2010 (6D) for SB507. Red diamonds represent the levels active urinary ceruloplasmin; Black circles represent urinary pregestagen concentrations; Pg=Progestagen; Pg=Progestagen; PEs=Proestrus; Es=Estrus; Numerical numbers=weeks of the luteal phase. Variations in the x and y axes exist to accommodate variable concentrations and durations. Data are weekly means ±SEM; n=2 reproductive cycles.

In the other female giant pandas examined, an increase in active urinary ceruloplasmin was observed for many cycles in which the animals were bred, primarily by AI, but no birth occurred. However, there were no ultrasound data to confirm these cycles as lost pregnancies, therefore we considered these cycles as suspected lost pregnancies based on ceruloplasmin. Similar to what was found in confirmed lost pregnancies, the pattern was different in these cycles compared to known term pregnancies (FIGS. 7A-B). While some of the suspected lost pregnancies were characterized as having a delayed increase in ceruloplasmin and/or a return of active ceruloplasmin to estrus/proestrus levels early in the luteal phase, all of the suspected lost pregnancies had deviations in the temporal pattern of urinary ceruloplasmin during the late luteal phase ($P \leqq 0:05$). These deviations included an early decrease in active ceruloplasmin during the secondary rise in progestagens and/or increases in active ceruloplasmin after the initial decline during the late luteal phase, when compared to term pregnancies (FIGS. 7A-D). Out of the 7seven total reproductive cycles in which animals were bred but no birth occurred, six cycles were confirmed or suspected lost pregnancies based on ceruloplasmin.

Figure 7:
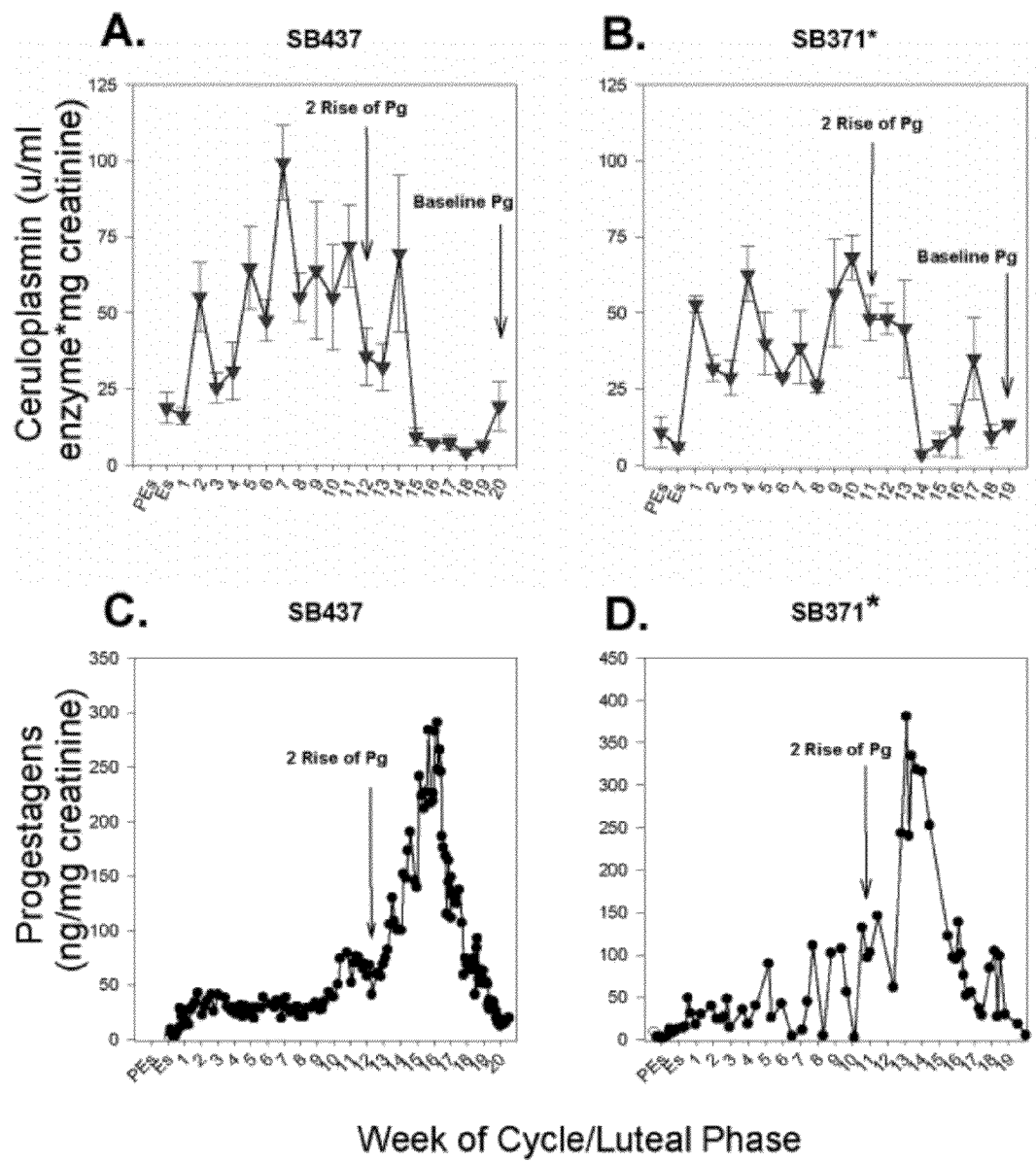
FIG. 7A-7D show representative patterns of active urinary ceruloplasmin and urinary progestagens in bred/no birth cycles for female giant pandas: suspected lost pregnancies based on ceruloplasmin.

FIG. 7 illustrates representative patterns of active urinary ceruloplasmin and urinary progestagens in bred/no birth cycles for female giant pandas: suspected lost pregnancies based on ceruloplasmin. The levels of active urinary ceruloplasmin in 2008 for SB437 (SNZP; Panel 7A) and 2001 for SB371 (SDZ; Panel 7B). Both animals were artificially inseminated. Panels 7C and D: The levels of urinary progestagen for SB437 in 2008 (7C) and for SB371 in 2001 (7D). Red diamonds represent the levels active urinary ceruloplasmin; Black circles represent urinary progestagen concentrations; Pg=Progestagen; PEs=Proestrus; Es=Estrus; Numerical numbers=weeks of the luteal phase. Variations in the x axis exist to accommodate variable concentrations and durations. Data are weekly means ±SEM; n=6 reproductive cycles, representative cycles (n=2) are presented herein. Samples from cycles obtained from SB371 were analyzed blind, without prior knowledge of cycle outcome. Because urinary progestagen concentrations for SB371 were analyzed using a different antibody, caution must be taken when directly comparing progestagen data between SB371 and the other animals. However, the same trends were observed in the relationship between active ceruloplasmin and progestagens in urine using both antibodies.

Figure 8:
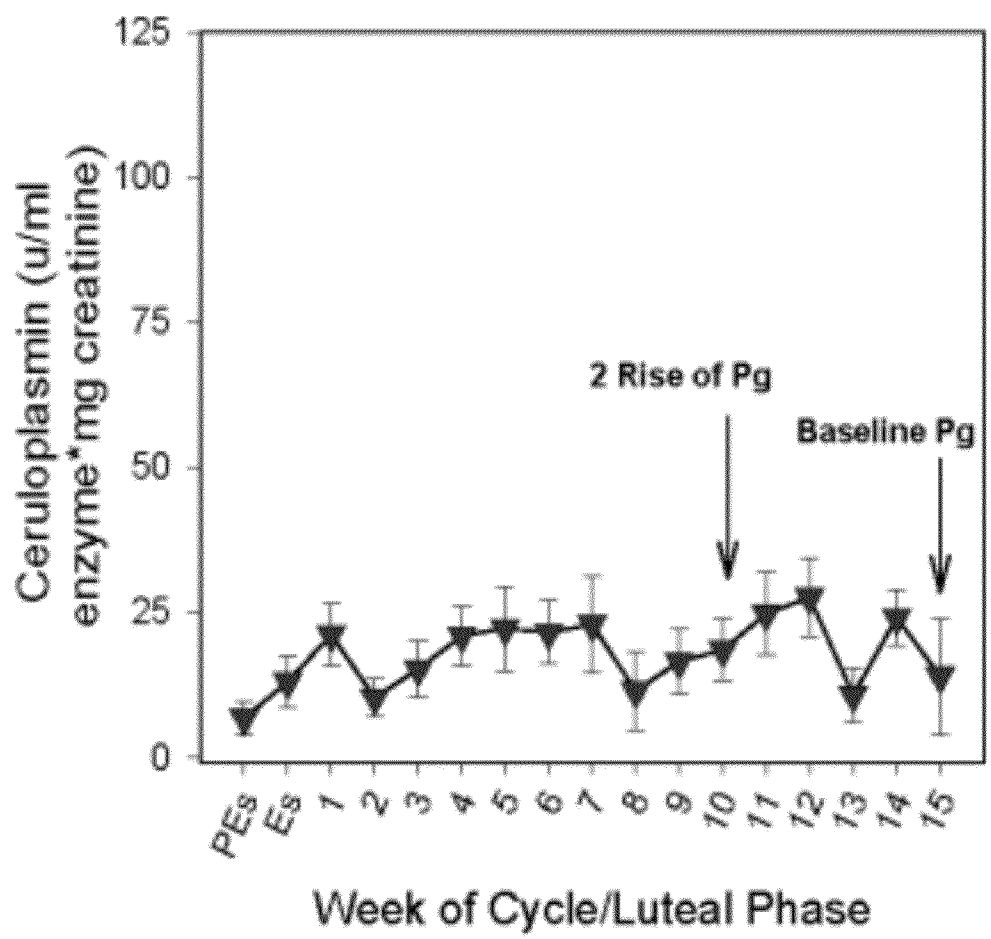
FIG. 8 shows the levels of active ceruloplasmin in urine for a bred/no birth cycle for female SB507: suspected pseudopregnancy/no conception or lost pregnancy that did not elicit an immune response based on ceruloplasmin.

In urine samples obtained from female SB507 (MZS) during the 2009 breeding season, no distinct increase in active ceruloplasmin was observed after AI (FIG. 8). Urinary progestagens were monitored to ensure a normal luteal phase (data not shown) but the levels of active ceruloplasmin in urine remained consistent throughout the luteal phase, similar to the levels that were observed at proestrus and estrus (FIG. 8); thus, the profile was most closely aligned to that of known pseudopregnant animals. Therefore, this cycle was considered a suspected pseudopregnancy/no conception or lost pregnancy that did not elicit an inflammatory response based on ceruloplasmin. This was the only cycle where a distinct increase in active urinary ceruloplasmin did not occur during the luteal phase out of the seven total reproductive cycles included in this study where animals were bred naturally or by AI but birth did not take place.

FIG. 8 illustrates the levels of active ceruloplasmin in urine for a bred/no birth cycle for female SB507: suspected pseudopregnancy/no conception or lost pregnancy that did not elicit an immune response based on ceruloplasmin. In 2009, SB507 (MZS) was artificially inseminated but no change in the levels of active urinary ceruloplasmin was observed throughout the luteal phase and levels were similar to those observed at proestrus and estrus. Pg=Progestagen; PEs=Proestrus; Es=Estrus; Numerical numbers=weeks of the luteal phase. Data are weekly means ±SEM; n=1 reproductive cycle.

In contrast, the modified CEP assay showed that in giant pandas active ceruloplasmin in urine increases within one week after conception, indicating that this species produces an inflammatory response well before implantation of the embryo (FIG. 2). Active urinary ceruloplasmin then remains elevated through approximately half of the secondary rise in progestagens (FIG. 3), with the secondary rise being the presumed time of implantation. However, because the secondary rise in progestagens occurs in both pregnant and pseudopregnant animals, the exact timing of implantation remains unknown in giant pandas.

Figure 9:
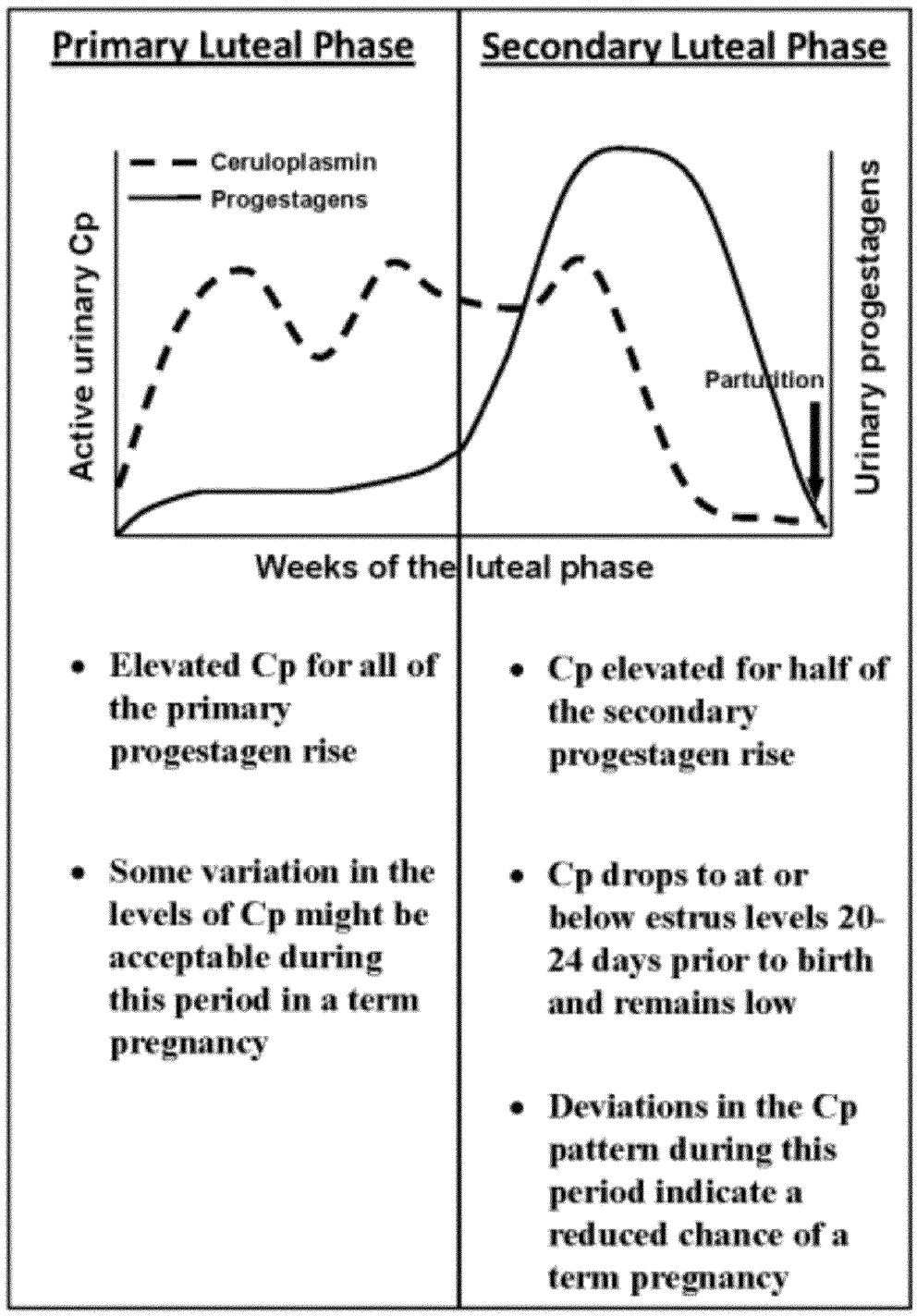
FIG. 9 illustrates the level of ceruloplasmin during primary luteal phase and secondary luteal phase.

This study also suggests that the rate of pregnancy loss among captive giant pandas is quite high. In the two confirmed lost pregnancies and in suspected lost pregnancies based on elevated ceruloplasmin, the pattern deviated from the profile observed in pregnancies carried to term particularly in the latter part of the luteal phase (FIGS. 2-5). In term pregnancies, ceruloplasmin remained elevated until approximately half way through the secondary rise and then decreased late in the luteal phase to at or below control levels for the remainder of the cycle. In contrast, while some of the lost pregnancies showed more variability in the pattern of urinary ceruloplasmin early in the luteal phase, all of the confirmed and suspected lost pregnancies based on ceruloplasmin showed abnormalities in the pattern of ceruloplasmin during the late luteal phase, compared to the term pregnancy profiles. All of the cycles that had elevated ceruloplasmin without a birth showed a deviation in the temporal pattern of change toward the end of the luteal phase by reaching baseline close to the onset of the secondary rise in progestagens (the presumed time of embryo implantation) and/or did not remain low after the primary decline to at or below estrus/proestrus levels that occurred 20-24 days before birth in the term pregnancies. A schematic summary of CEP assay results where elevated ceruloplasmin during the luteal phase was found is depicted in FIG. 9. Based on the results from this initial study, deviations in the pattern of urinary ceruloplasmin during the secondary rise suggest a reduced chance of a term pregnancy. Analysis of additional term and confirmed lost pregnancies will help to elucidate the importance of the temporal pattern of change in relation to term pregnancies compared to lost pregnancies in the giant panda.

Interestingly, in SB507's (MZS) 2009 cycle, no significant increase was observed in the levels of active ceruloplasmin in urine during the luteal phase, indicating that this cycle may have been a pseudopregnancy when analyzing the cycle based on ceruloplasmin (FIG. 6). However, it is also possible that this cycle was a lost pregnancy that did not elicit an appropriate inflammatory or immune response. In other species, there is evidence that immunological recognition is important for the maintenance of pregnancy and that an inappropriate maternal response to the fetus can result in fetal death. A failed increase in, or an abnormal pattern of, active ceruloplasmin in urine following breeding or AI may be characteristic of an inappropriate response to pregnancy by the maternal immune system. Moreover, an unusual ceruloplasmin profile could also be a sign of abnormal embryonic development. No studies examining the specific temporal pattern of change in ceruloplasmin during pregnancy in relation to fetal loss have been carried out in other species. However, there is some evidence that either lower or higher levels of ceruloplasmin compared to levels observed during normal pregnancy could be an indication of problems associated with gestation in humans. Abnormal levels of ceruloplasmin have been found in blood and/or in amniotic fluid during pregnancies which resulted in such conditions as spontaneous abortions, preeclampsia, and Klinefelter's syndrome.

EXAMPLE 2

Figure 10:
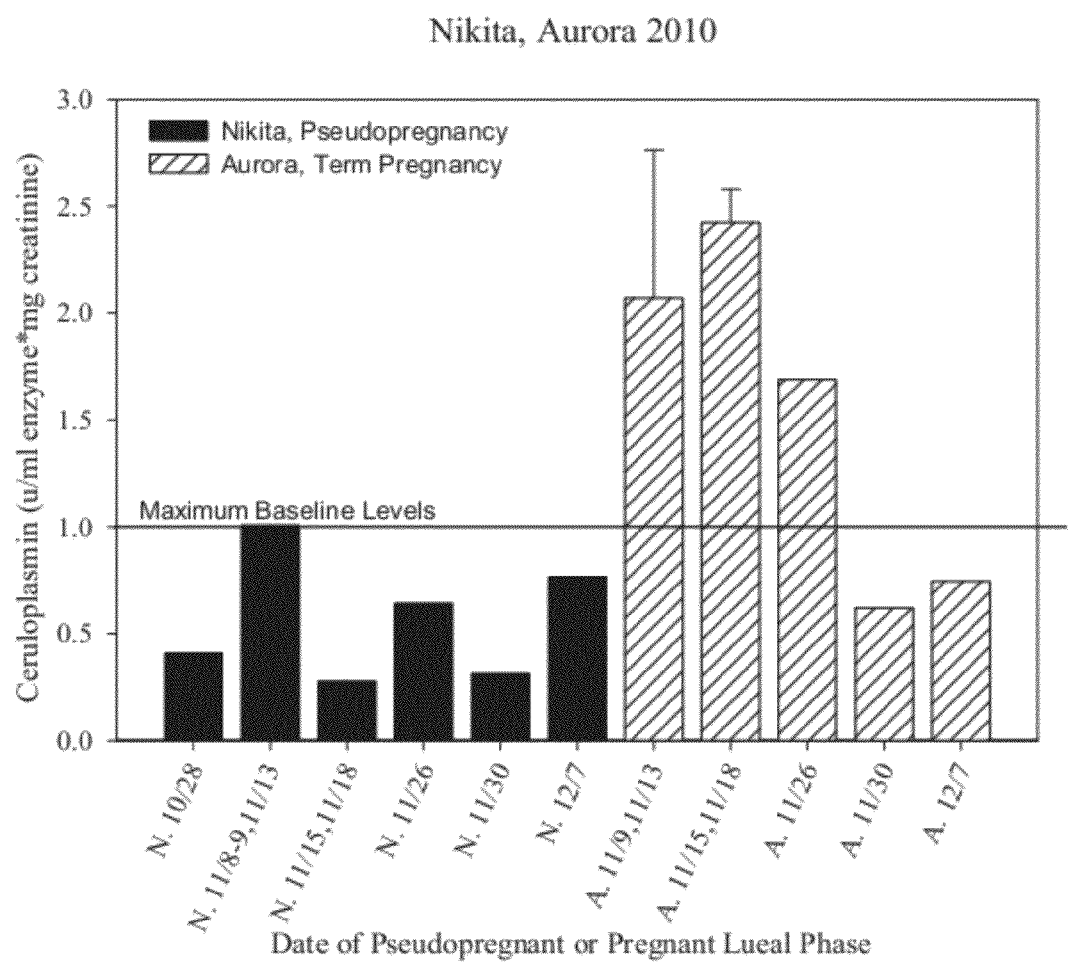
FIG. 10 is the preliminary results of the levels of urinary ceruloplasmin during the luteal phase in pseudopregnant female polar bear.

FIG. 10. Preliminary results of the levels of urinary ceruloplasmin during the luteal phase in a pseudopregnant female polar bear (Nikita) and a pregnant female polar bear which resulted in the birth of cubs (Aurora) after breeding. Compared to giant pandas, preliminary results indicate that in polar bears the basal levels of urinary Cp are much lower, at around 1 u and below. In Nikita, the maximum baseline Cp levels did not exceed 1 u during the luteal phase, suggesting that she was experiencing a pseudopregnancy (no birth of cubs occurred). However in Aurora, the confirmed pregnant female (pregnancy was confirmed by the birth of cubs), Cp was often elevated in during the pregnant luteal phase.

Figure 11:
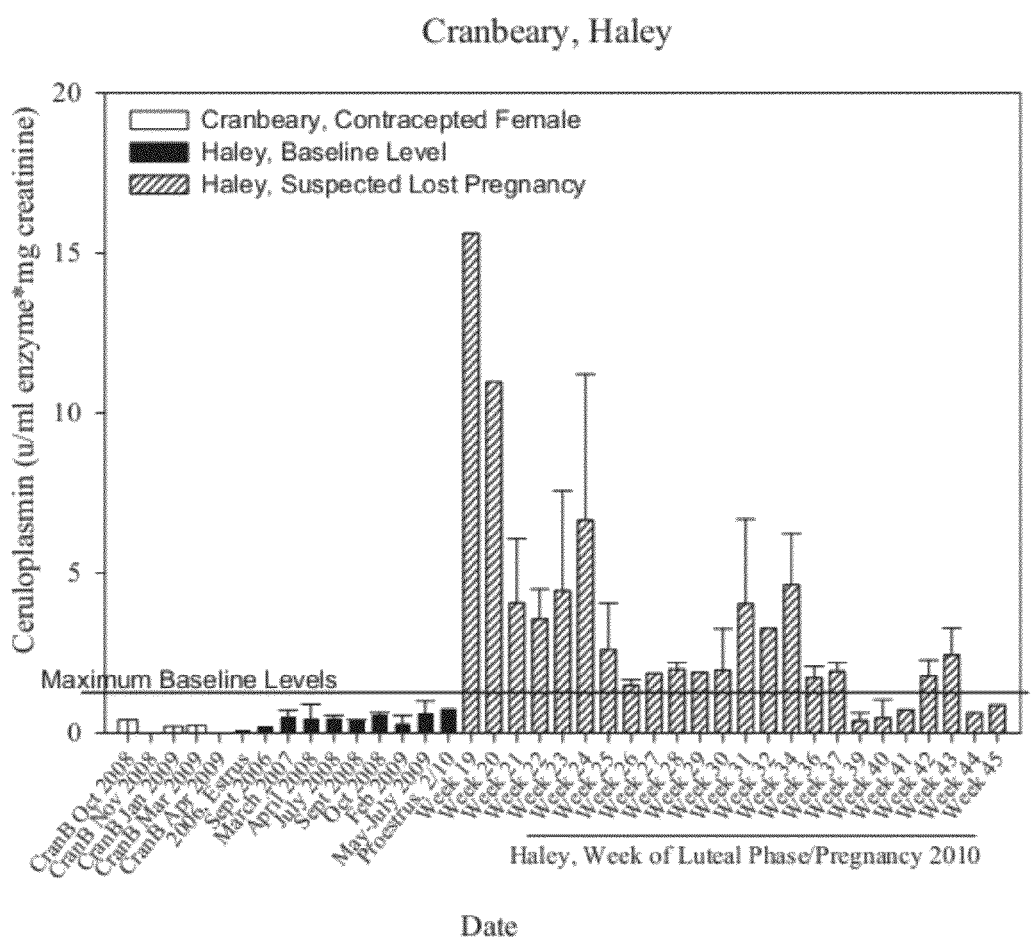
FIG. 11 is the preliminary results of the levels of urinary ceruloplasmin in a female polar bear on contraception (Cranbeary) and in a female polar bear at various dates without breeding (for baseline validation) and during the luteal phase after breeding.

Referring to FIG. 11 that is the preliminary results of the levels of urinary ceruloplasmin in a female polar bear on contraception (Cranbeary) and in a female polar bear at various dates without breeding (for baseline validation) and during the luteal phase after breeding (Haley). Maximum baseline Cp levels did not exceed 1 u in Cranbeary, the female on contraception, and at all dates in which no breeding had taken place for Haley. After breeding in 2010, Haley exhibited elevated levels of Cp during the luteal phase, suggesting that she may have experienced a lost pregnancy. Unfortunately, the majority of captive polar bears are not trained to accept ultrasound procedures. Therefore to date, ultrasound cannot be used to help confirm lost pregnancies in this species.

Figure 12:
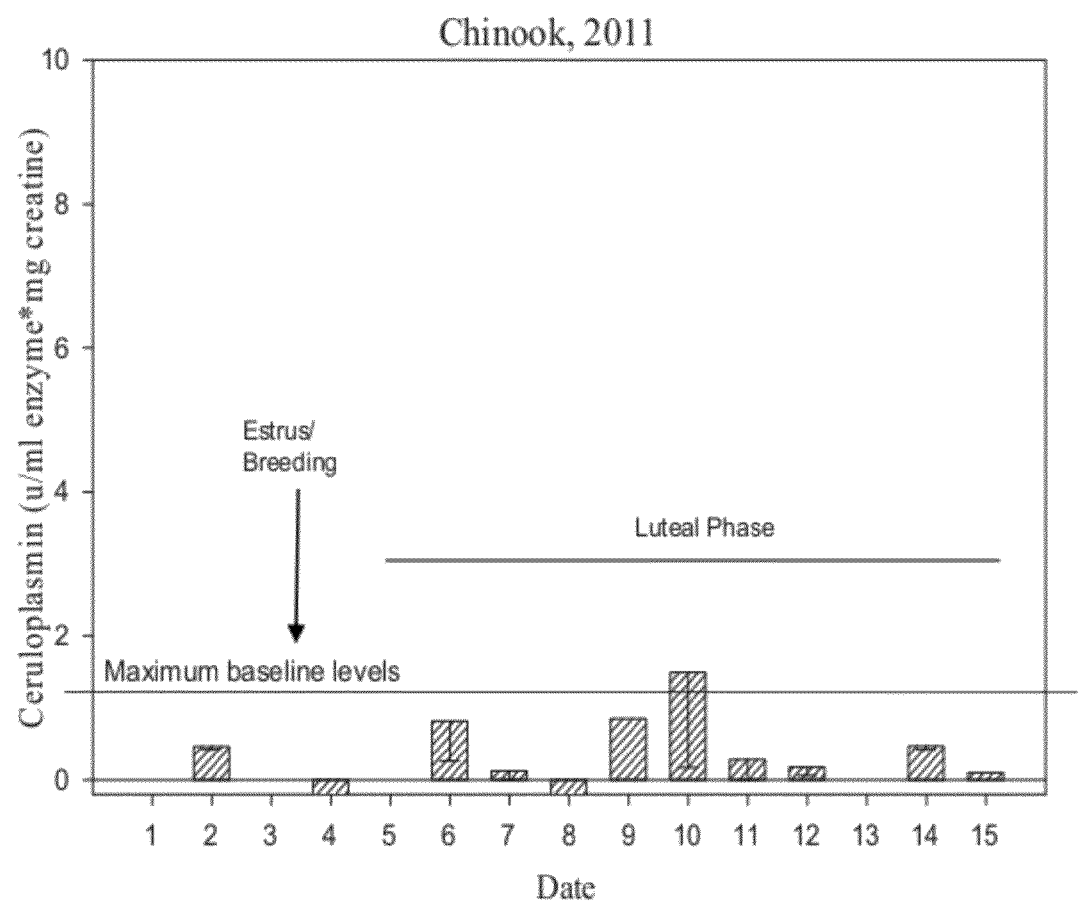
FIG. 12 is the preliminary results of the levels of urinary ceruloplasmin in a female polar bear before, during and after breeding (Chinook).

Now referring to FIG. 12 which is the reliminary results of the levels of urinary ceruloplasmin in a female polar bear before, during and after breeding (Chinook). Maximum baseline Cp levels did not exceed 1 u in Chinook before breeding. During the luteal phase, Cp levels also remained extremely low during the weeks collected, suggesting that the female was not pregnant. This cycle did not result in the birth of cubs.

These data provide a foundation for understanding conception, fetal loss, and recognition and maintenance of pregnancy in giant pandas. The method disclosed on this invention will provide a background for future research in other endangered carnivores and ursids, such as the polar bear, in which common physiological factors are unreliable at determining pregnancy and the understanding of many components of basic reproductive biology is lacking.

EXAMPLE 3

Ceruloplasmin Colorimetric Activity Kit

Ceruloplasmin Activity Kit is designed to quantitatively measure ceruloplasmin activity in urine samples. A human ceruloplasmin standard is provided to generate a standard curve for the assay and all samples should be read off of the standard curve. Samples are diluted in the provided Assay Buffer and added to the wells of a half area clear plate. The reconstituted Ceruloplasmin Substrate is added and the plate is incubated at 30° C. for 60 minutes. The ceruloplasmin in the standards and samples reacts with the substrate to produce a colored product. The optical density is read at 560 nm. Increasing levels of ceruloplasmin in the samples causes an increase in the fuschia (pinkpurple) product. The activity of the ceruloplasmin in the sample is calculated after making a suitable correction for any dilution, using software available with most plate readers. The results are expressed in terms of units of ceruloplasmin activity per mL.

Supplied Components: Clear 96 well Half Area Plates 2 Plates, Ceruloplasmin Standard 20 µL; 1,000 Units/mL of human ceruloplasmin in a special stabilizing solution; Assay Buffer Concentrate 28 mL A 5× concentrate containing detergents and stabilizers; Ceruloplasmin Colorimetric Substrate 2 Vials, Ceruloplasmin substrate lyophilized from a special stabilizing solution; and Plate Sealers 2 Each.

Storage Instructions: This kit should be stored at −20° C. until the expiration date of the kit. Once opened the kit can be stored at 4° C. up to the expiration date on the kit label, except for the ceruloplasmin. Standard and reconstituted Ceruloplasmin Substrate, which must be stored at −20° C. Repeater pipet with disposable tips capable of dispensing 25 µL. An incubator capable of maintaining 30° C., 96 well plate reader capable of reading optical density at 560 nm. Software for converting optical density readings from the plate reader and carrying out four parameter logistic curve (4PLC) fitting. Contact your plate reader manufacturer for details.

Sample Types and Preparation; Samples that need to be stored after collection should be stored at −70° C. or lower, preferably after being frozen in liquid nitrogen. This assay has been validated for urine samples. Samples containing visible particulate should be centrifuged prior to using. Ceruloplasmins are ancient enzymes that should behave in a similar manner to the colorimetric substrate. It is believed that the assay will measure Cp activity from a wide range of sources. It is up to the end user to determine if their samples can be measured using this assay.

Assay Protocol: 1. Pre-warm incubator to 30° C.; 2. Pipet 100 µL of diluted samples or appropriate standards into duplicate wells in the plate; 3. Pipet 100 µL of Assay Buffer into duplicate wells as the Zero standard.; 4. Add 25 µL of the reconstituted Cp Substrate solution to each well using a repeater pipet; 5. Incubate at 30° C. for 60 minutes; 6. Read the optical density generated from each well in a plate reader capable of reading at 560 nm.

Allow the kit reagents to come to room temperature for 30-60 minutes. We recommend that all standards and samples be run in duplicate to allow the end user to accurately determine Ceruloplasmin activities. Ensure that all samples have reached room temperature and have been diluted as appropriate prior to running them in the kit.

Assay Buffer: Dilute Assay Buffer Concentrate 1:5 by adding one part of the concentrate to four parts of deionized water. Once diluted this is stable at 4° C. for 3 months.

Standard Preparation: Standards are prepared by labeling seven tubes as #1 through #7. Add 995 µL of Assay Buffer to tube #1. Pipet 300 µL of Assay Buffer into tubes #2 to #7. Carefully add 5 µL of the Ceruloplasmin Stock from the vial to tube #1 and vortex completely. Take 600 µL of the Cp solution in tube #1 and add it to tube #2 and vortex completely. Repeat the serial dilutions for tubes #3 through #7. The ceruloplasmin activity in tubes 1 through 8 will be 5, 3.33, 2.22, 1.48, 0.988, 0.658, and 0.439 U/mL.

Ceruloplasmin Substrate Preparation: Add 3 mL of water to the vial and mix thoroughly. This solution can be stored at 4° C. for up to 2 weeks. The solution can also be stored at −20° C. for up to the expiration date on the kit label.

Assay Protocol: Use the plate layout sheet on the back page to aid in proper sample and standard identification. Set plate parameters for a 96-well Corning Costar 3695 plate. 1. Pre-warm incubator to 30° C.; 2. Pipet 100 µL of diluted samples or appropriate standards into duplicate wells in the plate; 3. Pipet 100 µL of Assay Buffer into duplicate wells as the Zero standard; 4. Add 25 µL of the reconstituted Cp Substrate solution to each well using a repeater pipet; 5. Incubate at 30°

C. for 60 minutes; 6. Read the optical density generated from each well in a plate reader capable of reading at 560 nm.

Calculation of Results: Average the duplicate OD readings for each standard and sample. Create a standard curve by reducing the data using the 4PLC fitting routine on the plate reader, after subtracting the mean OD for the zero standard. The sample activity obtained should be multiplied by the dilution factor to obtain neat sample values.

TABLE 2

Typical Data

| Sample | Mean Net OD | Ceruloplasmin Activity (U/mL) |
|---|---|---|
| Standard 1 | 0.922 | 5 |
| Standard 2 | 0.663 | 3.33 |
| Standard 3 | 0.428 | 2.22 |
| Standard 4 | 0.290 | 1.48 |
| Standard 5 | 0.152 | 0.988 |
| Standard 6 | 0.108 | 0.658 |
| Standard 7 | 0.049 | 0.439 |
| Zero | 0.000 | 0 |
| Sample 1 | 0.337 | 1.831 |
| Sample 2 | 0.209 | 1.169 |

Ceruloplasmin Unit Definition: One Unit of Ceruloplasmin causes an increase in OD of 0.01 per minute at 37° C. and pH 5.5 using N,N-dimethyl-p-phenylene diamine as substrate.

Validation Data

Sensitivity: Sensitivity was calculated by comparing the ODs for twenty wells run for each of the zero and standard #7. The detection limit was determined at two (2) standard deviations from the zero along the standard curve. Sensitivity was determined as 0.242 U/mL. This is equivalent to 24.2 mU/well.

Limit of Detection: The Limit of Detection for the assay was determined in a similar manner by comparing the ODs for twenty runs for each of the zero standard and a low concentration panda urine sample. Limit of Detection was determined as 0.425 mU/mL. This is equivalent to 42.5 mU/well.

Linearity: Linearity was determined by taking two diluted panda urine samples, one with a high known ceruloplasmin activity of 2.47 U/mL and the other with a lower ceruloplasmin activity of 0.60 U/mL and mixing them in the ratios given below. The measured activities were compared to the expected values based on the ratios used.

TABLE 3

| High Sample | Low Sample | Observed Activity (U/mL) | Expected Activity (U/mL) | % Recovery |
|---|---|---|---|---|
| 80% | 20% | 2.22 | 2.10 | 105.5 |
| 60% | 40% | 1.77 | 1.72 | 102.6 |
| 40% | 60% | 1.57 | 1.35 | 116.5 |
| 20% | 80% | 0.97 | 0.97 | 99.5 |
| | | | Mean Recovery | 106.0% |

Intra Assay Precision: Two panda urine samples diluted in Assay Buffer were run in replicates of 20 in an assay. The mean and precision of the calculated activities were:

TABLE 4

| Sample | Ceruloplasmin Activity (U/mL) | % CV |
|---|---|---|
| 1 | 1.85 | 5.0 |
| 2 | 1.17 | 7.1 |

Inter Assay Precision: Two panda urine samples diluted in Assay Buffer were run in duplicates in sixteen assays run over multiple days by three operators. The mean and precision of the calculated activities were:

TABLE 5

| Sample | Ceruloplasmin Activity (U/mL) | % CV |
|---|---|---|
| 1 | 1.92 | 8.7 |
| 2 | 1.17 | 12.2 |

EXAMPLE 4

Figure 13:
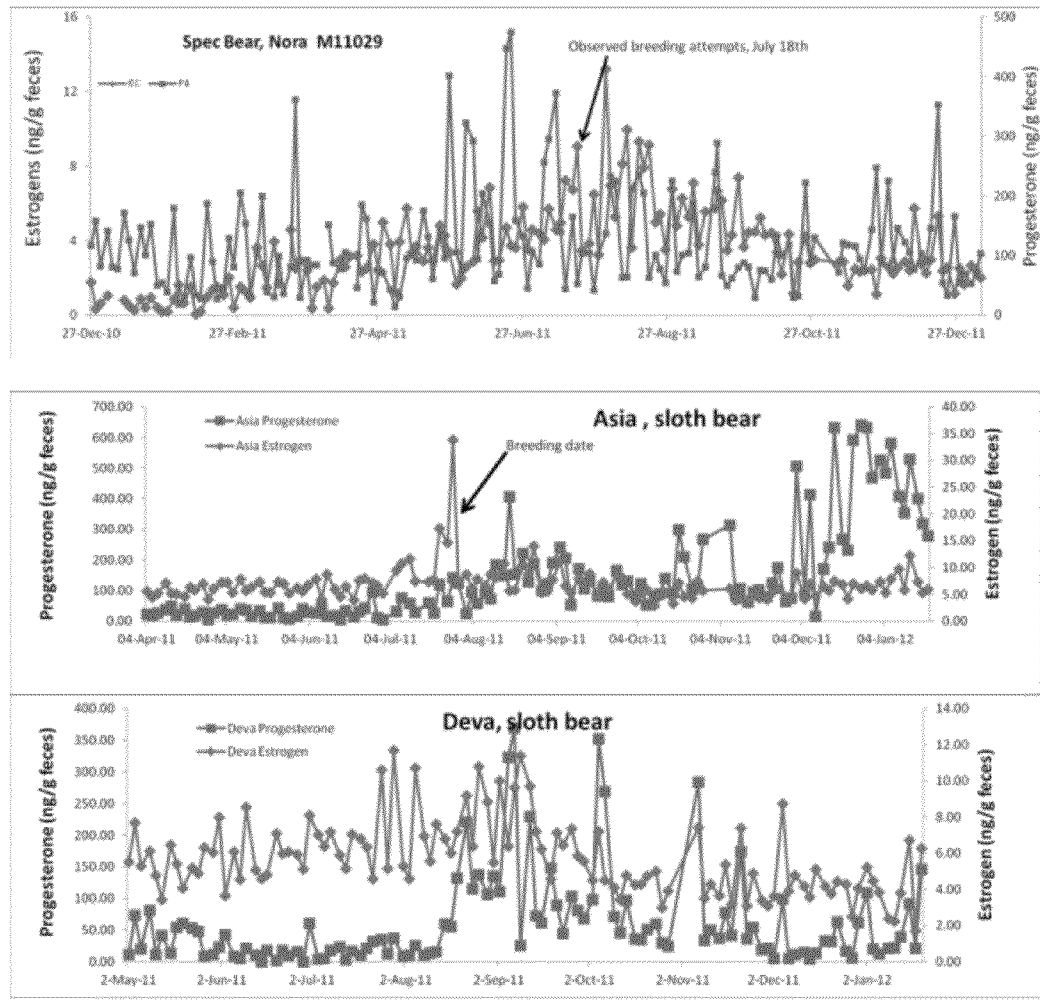
FIG. 13 Fecal metabolites of estrogen and progesterone for 2 Sloth bears and 1 Spectacled bear FIG. 14 A preliminary evaluation of ceruloplasmin activity in the urine of a Spectacled bear and a Sloth bear after observed breeding and elevated estrogen value.
Figure 14:
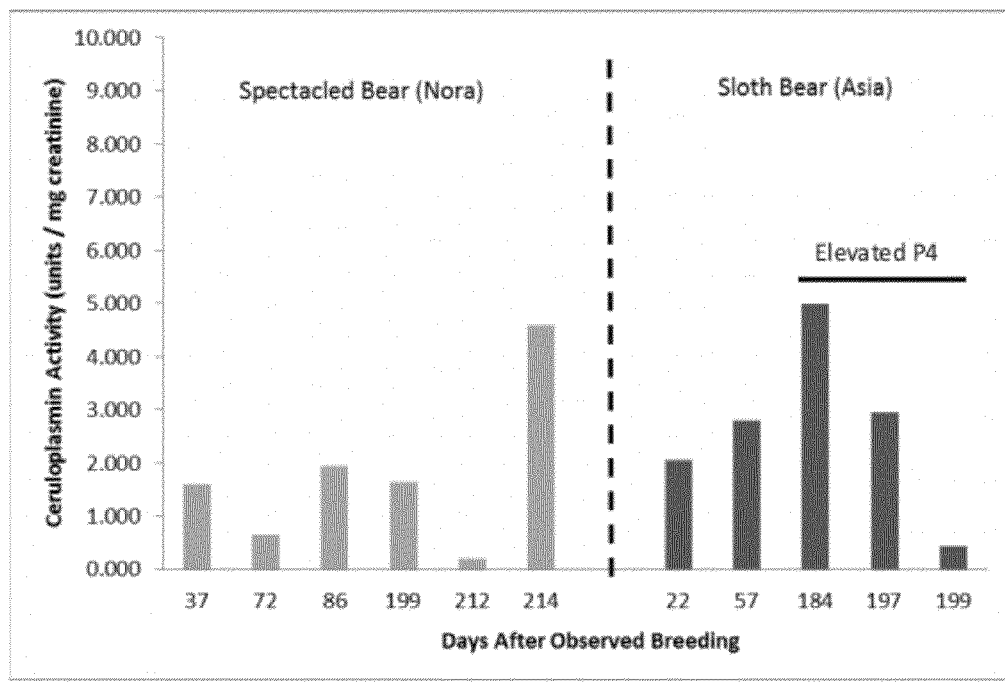

Now referring to FIG. 13 and FIG. 14. FIG. 13 illustrates the fecal metabolites of estrogen and progesterone for 2 Sloth bears (Asia and Deva) and 1 Spectacled bear (Nora) held at the Cleveland Metroparks Zoo. Elevated estrogen values and observed breeding (indicating estrous) are noted with an arrow. An elevation of fecal progesterone occurred ~120 days after observed breeding events for Asia indicating a suspected secondary luteal phase/pseudopregnancy. None of the bears gave birth to cubs. FIG. 14 shows a preliminary evaluation of ceruloplasmin activity in the urine of a Spectacled bear (Nora, age 20 years) and a Sloth bear (Asia, age 10 years) after observed breeding and elevated estrogen value. An increase in ceruloplasmin activity was observed in both species >150 days after breeding. In particular, elevated ceruloplasmin activity increased during the suspected secondary luteal phase rise in progesterone in the Sloth bear (Asia). No samples were available prior to breeding, but baseline ceruloplasmin activity values are expected to <1 unit/mg creatinine in these species based on the values occurring close to estrous. Evaluation of the temporal and synchronous relationships between fecal progesterone and ceruloplasmin activity, and their use as pregnancy biomarkers in Spectacled and Sloth bears are ongoing.

EXAMPLE 5

Figure 15:
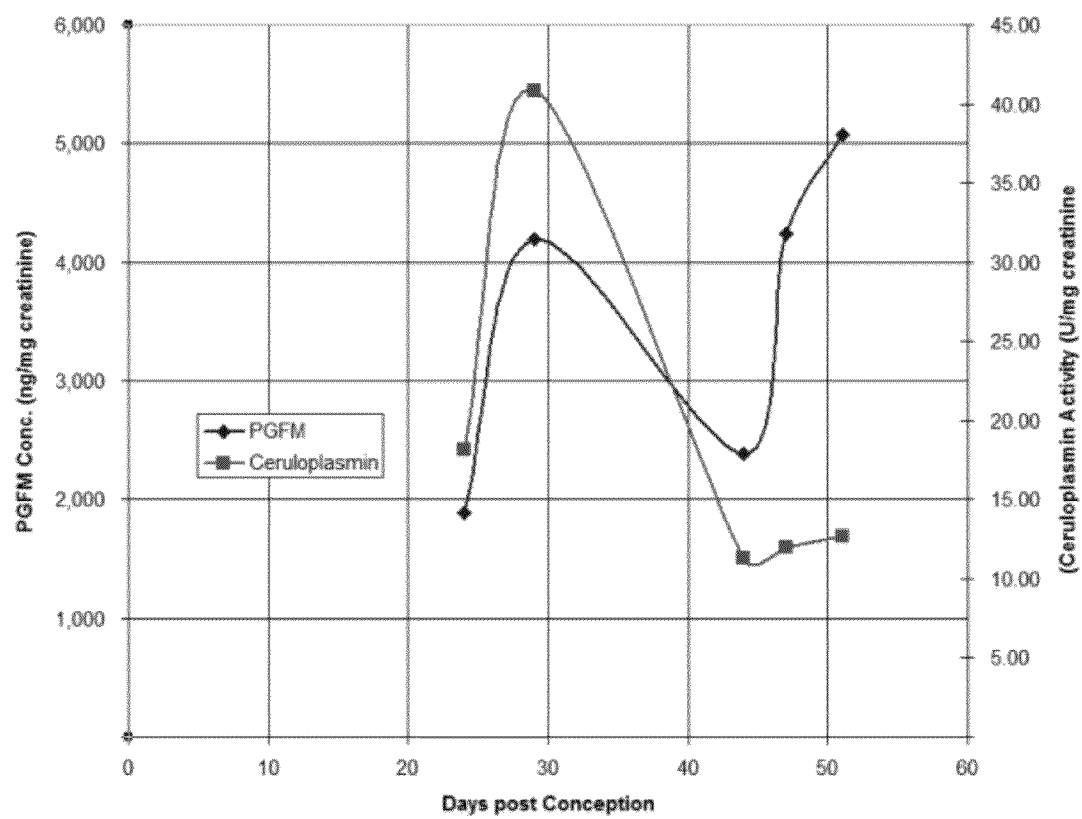
FIG. 15 is the ceruloplasmin activity in the urine of lynx.

Now referring to FIG. 15 that illustrates shows ceruloplasmin activity in the urine of a lynx. FIG. 15 has the data from urine samples from Iberian Lynx at the Leibniz Institute for Zoo and Wildlife Research, Berlin. One of these lynx was pregnant and the urine was tested for PGFM (13,14,Dihydro-15-keto-Prostaglandin F2alpha), Cp activity using assay described in Example 3 and urine creatinine assay from Arbor Assays. The PGFM and Cp results were normalized to the creatinine data (as a way to normalize for urinary volume). FIG. 15 shows that there is a correlation between PGFM values and Cp activity. PGEM is a know pregnancy marker in lynx. FIG. 15 indicates that a relationship between PGFM and Cp activity at least in the early phase of the pregnancy.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

REFERENCES

MacIntyre G, Gutfreund K S, Martin W R W Martin, Camicioli R, Cox D W (2004) Value of an en enzymatic assay for the determination of serum ceruloplasmin. J Lab Clin Med 144:294-301.

Merle U, Eisenbach C, Weiss K H, Tuma S, Stremmel W (2009) Serum ceruloplasmin oxidase activity is a sensitive and highly specific diagnostic marker for Wilson's disease: J Hepatol 51:925-930.

Sunderman F W, Jr., Nomoto S (1970) Measurement of human serum ceruloplasmin by its p-phenylenediamine oxidase activity. Clin Chem 16: 903-910.

Burrows S, Pekala B (1971) Serum copper and ceruloplasmin in pregnancy. Am J Obstet Gynecol 109: 907-909.

Markowitz H, Gubler C J, Mahoney J P, Cartwright G E, Wintrobe M M (1955) Studies on copper metabolism. XIV. Copper, ceruloplasmin and oxidase activity in sera of normal human subjects, pregnant women, and patients with infection, hepatolenticular degeneration and the nephrotic syndrome. J Clin Invest 34: 1498-1508.

Ulutas P A, Musal B, Kiral F, Bildik A (2009) Acute phase protein levels in pregnancy and oestrus cycle in bitches. Res Vet Sci 86: 373-376.

Vannucchi C I, Mirandola R M, Oliveira C M (2002) Acute-phase protein profile during gestation and diestrous: proposal for an early pregnacy test in bitches. Anim Reprod Sci 74: 87-99.

Willis E L, Kersey D C, Durrant B S, Kouba A J. 2011. The acute phase protein ceruloplasmin as a non-invasive marker of pseudopregnancy, pregnancy, and pregnancy loss in the giant panda. PLoS One 6: e211549. Doi: 10.1371/journal.pone.0021159

Holmberg C G and Laurell C B. Investigation serum copper. II. Isolation of the copper containing protein, and a description of some its properties. 1948, Acta. Chem. Scand. 2:550-556. Malmstrom B G. Enzymology of oxygen. Annu. Rev. Biochem. 1982, 51: 21-59.

Farver O. and Pecht I. Electron transfer reactions in multi-copper oxidases. In: Multi-Copper Oxidases, 1997, pp. 355-389, Messerschmidt A. (ed.), World Scientific Publication, Singapore.

Harris, Z L and Gitlin, J D, Genetic and molecular basis for copper toxicity, Am. J. Clin. Nutr. 1996, 63:836S-841S.

Yoshida K., . et al. A mutation in the ceruloplasmin gene is associated with systemic hemosiderosis in humans. Nat. Genet. 1995, 9:267-272.

Harris Z L., Takahashi Y., Miyajima H., Serizawa M., MacGillivray R T A. and Gitlin J D. Aceruloplasminemia: molecular characterization of a novel disorder of iron metabolism. Proc. Natl. Acad. Sci. USA, 1995, 92:2539-2543.

Takahashi Y., Miyajima H., Shirabe S., Nagataki S., Suenaga, A. and Gitlin J D. Characterization of a nonsense utation in the ceruloplasmin gene resulting in diabetes and neurode-generative disease. 1996, Hum. Mol. Genet. 5:81-84.

Fields, M., Lewis, C., Scholfield, D., Powel, A S., Rose, A J., Reiser, S., and Smith, J C., Female rats are protected against the fructose-induced mortality of copper deficiency. Proc. Soc. Expl Biol. Med. 1986, I86:145-I49.

IUCN/SSC (2010) 2010 Breeding Strategy Recommendations and Summary of the Status of the Giant Panda Captive Population. Chengdu, China.

Chaudhuri M, Kleiman D G, Wildt D E, Bush M, Frank E S, et al. (1988) Urinary steroid concentrations during natural and gonadotrophin-induced oestrus and pregnancy in the giant panda (Ailuropoda melanoleuca). J Reprod Fertil 84: 23-28.

Monfort S L, Dahl K D, Czekala N M, Stevens L, Bush M, et al. (1989) Monitoring ovarian function and pregnancy in the giant panda (Ailuropoda melanoleuca) by evaluating urinary bioactive FSH and steroid metabolites. J Reprod Fertil 85: 203-212.

Steinman K, Monfort S L, McGeehan L, Kersey D, Gual-Sil F, et al. (2006) Endocrinology of the giant panda and application of hormone technology to species management. In: Wildt D E, Zhang A, Zhang D, Janssen D L, Ellis S, editors. Giant pandas: biology, veterinary medicine and management. Cambridge: Cambridge University Press. pp. 198-230.

Kersey D C, Wildt D E, Brown J L, Snyder R J, Huang Y, et al. (2010) Unique biphasic progestagen profile in parturient and non-parturient giant pandas (Ailuropoda melanoleuca) as determined by faecal hormone monitoring. Reproduction 140: 183-193.

Kersey D C, Wildt D E, Brown J L, Snyder R J, Huang Y, et al. (2010) Endocrine milieu of perioestrus in the giant panda (Ailuropoda melanoleuca), as determined by non-invasive hormone measures. Reprod Fertil Dev 22: 901-912.

Zhang H, Li. D, Wang C, Hull V (2009) Delayed implantation in giant pandas: The first comprehensive empirical evidence. Reproduction 138: 979-986.

Sutherland-Smith M, Morris P J, Silverman S (2004) Pregnancy detection and fetal monitoring via ultrasound in a giant panda (Ailuropoda melanoleuca). Zoo Biol 23: 449-461.

Hodges J, Bevan J, Celma M, Hearn J, Jones D, et al. (1984) Aspects of the reproductive endocrinology of the female Giant panda (Ailuropoda melanoleaca) in captivity with special reference to the detection of ovulation and pregnancy. Zoo Biol 203: 253-267.

Hildebrandt T B, Brown J L, Jewgenow K, Goeritz F (2006) Use of ultrasound to study and augment reproduction in the giant panda. In: Wildt D E, Lindburg D, editors. Biology of the Giant Panda. Cambridge, UK: Cambridge University Press. pp. 410-439.

Durrant B S, Ravida N, Spady T, Cheng A (2006) New technologies for the study of carnivore reproduction. Theriogenology 66: 1729-1736.

Steinetz B G, Brown J L, Roth T L, Czekala N (2005) Relaxin concentrations in serum and urine of endangered species: correlations with physiologic events and use as a marker of pregnancy. Ann NY Acad Sci 1041: 367-378.

Vannucchi C I, Mirandola R M, Oliveira C M (2002) Acute-phase protein profile during gestation and diestrous: proposal for an early pregnacy test in bitches. Anim Reprod Sci 74: 87-99.

Markowitz H, Gubler C J, Mahoney J P, Cartwright G E, Wintrobe M M (1955) Studies on copper metabolism. XIV. Copper, ceruloplasmin and oxidase activity in sera of normal human subjects, pregnant women, and patients with infection, hepatolenticular degeneration and the nephrotic syndrome. J Clin Invest 34: 1498-1508.

Burrows S, Pekala B (1971) Serum copper and ceruloplasmin in pregnancy. Am J Obstet Gynecol 109: 907-909.

Ulutas P A, Musal B, Kiral F, Bildik A (2009) Acute phase protein levels in pregnancy and oestrus cycle in bitches. Res Vet Sci 86: 373-376.

Ellis S, Pan W, Xie Z, Wildt D (2006) The giant panda as a social, biological and conservation phenomenon. In: Wildt D E Z A, Zhang H, Janssen D L, Ellis S. editor. Giant Pandas: Biology, Veterinary Medicine and Management Cambridge, UK; Cambridge University Press. pp. 1-16.

Denko C W (1979) Protective role of ceruloplasmin in inflammation. Agents Actions 9: 333-336.

Goldstein I M, Kaplan H B, Edelson H S, Weissmann G (1979) A new function for ceruloplasmin as an acute-phase reactant in inflammation: a scavenger of superoxide anion radicals. Trans Assoc Am Physicians 92: 360-369.

Holmberg C G, Laurell C B (1948) Investigations in serum copper. II. Isolation of the copper-containing protein and a description of some of its properties. Acta Chemica Scandinavica. 2: 550-556.

Wisdom S J, Wilson R, McKillop J H, Walker J J (1991) Antioxidant systems in normal pregnancy and in pregnancy-induced hypertension. Am J Obstet Gynecol 165: 1701-1704.

Osaki S, Johnson D A, Frieden E (1966) The possible significance of the ferrous oxidase activity of ceruloplasmin in normal human serum. J Biol Chem 241: 2746-2751.

Komlos L, Klein T, Korostishevsky M (2007) HLA-A2 class I antigens in couples with recurrent spontaneous abortions. Int J Immunogenet 34: 241-246.

Toder V, Strassburger D, Carp H, Irlin Y, Lurie S, et al. (1989) Immunopotentiation and pregnancy loss. J Reprod Fertil Suppl 37: 79-84.

Tangri S, Raghupathy R (1993) Expression of cytokines in placentas of mice undergoing immunologically mediated spontaneous fetal resorptions. Biol Reprod 49: 850-856.

Zigril M, Fein A, Carp H, Toder V (1991) Immunopotentiation reverses the embryotoxic effect of serum from women with pregnancy loss. Fertil Steril 56: 653-659.

Robertson S A, Mau V J, Hudson S N, Tremellen K P (1997) Cytokine-leukocyte networks and the establishment of pregnancy. Am J Reprod Immunol 37: 438-442.

Savion S, Zeldich E, Orenstein H, Shepshelovich J, Torchinsky A, et al. (2002) Cytokine expression in the uterus of mice with pregnancy loss: effect of maternal immunopotentiation with GM-CSF. Reproduction 123: 399-409.

Komlos L, Zamir R, Joshua H, Halbrecht I (1977) Common HLA antigens in couples with repeated abortions. Clin Immunol Immunopathol 7: 330-335.

Jenkins C, Wilson R, Roberts J, Miller H, McKillop J H, et al. (2000) Antioxidants: their role in pregnancy and miscarriage. Antioxid Redox Signal 2: 623-628.

Anagnostopoulos A K, Kolialexi A, Mavrou A, Vougas K, Papantoniou N, et al. (2010) Proteornic analysis of amniotic fluid in pregnancies with Klinefelter syndrome foetuses. J Proteomics 73: 943-950.

Fattah M M, Ibrahim F K, Ramadan M A, Sammour M B (1976) Ceruloplasmin and copper level in maternal and cord blood and in the placenta in normal pregnancy and in pre-eclampsia. Acta Obstet Gynecol Scand 55: 383-385.

Griffin J F (1983) Pregnancy-associated plasma protein levels at term in normal pregnancy, preeclampsia and essential hypertension. Aust N Z J Obstet Gynaecol 23: 11-14.

Serdar Z, Gur E, Develioglu O (2006) Serum iron and copper status and oxidative stress in severe and mild preeclampsia. Cell Biochem Funct 24: 209-215.

Tsubota T, Kanagawa H, Mano T, Aoi T (1990) Corpora albicantia and placental scars in the hokkaido brown bear. International Conference on Bear Research and Management 8: 125-128.

Dehnhard M, Hildebrandt T B, Knauf T, Jewgenow K, Kolter L, et al. (2006) Comparative endocrine investigations in three bear species based on urinary steroid metabolites and volatiles. Theriogenology 66: 1755-1761.

Goritz F, Hildebrandt T, Jewgenow K, Wagner N, Hermes R, et al. (1997) Transrectal ultrasonographic examination of the female urogenital tract in nonpregnant and pregnant captive bears (Ursidae). J Reprod Fertil Suppl 51: 303-312.

Sunderman F W, Jr., Nomoto S (1970) Measurement of human serum ceruloplasmin by its p-phenylenediamine oxidase activity. Clin Chem 16: 903-910.

Curzon G, Vallet L (1960) The purification of human caeruloplasmin. Biochem J 74: 279-287. Taussky H H (1954) A microcolorimetric determination of creatine in urine by the Jaffe reaction. J Biol Chem 208: 853-861.

Hartley H O (1950) The maximum F-ratio as a short-cut test for heterogeneity of variance. Biometrika 37: 308-312.

Neter J. W W, Kutner M. H. (1985) Applied linear statistical models: regression, analysis of variance, and experimental designs. Homewood, Ill.: R. D. Irwin.

The invention claimed is:

1. A method for detection of pregnancy by evaluating at least one urine sample for ceruloplasmin from a mammalian test subject comprising the steps of:
   a. collecting at least one fresh urine sample from a test subject;
   b. adding a substrate specific to ceruloplasmin to said at least one urine sample;
   c. measuring oxidase activity of said ceruloplasmin through a sequential reading of optical density for oxidase activity of ceruloplasmin using a spectrophotometer to determine the concentration of ceruloplasmin in said at least one urine sample;
   d. determining the base line level oxidase activity of ceruloplasmin from a nonpregnant mammal of the same species; and
   e. determining an elevated level of said oxidase activity of ceruloplasmin in said urine sample greater than that of the baseline level of said oxidase activity of ceruloplasmin from a nonpregnant mammal of the same species, said elevated level of said oxidase activity ceruloplasmin in the said urine sample being indicative of pregnancy.

2. The method in claim 1 wherein the ceruloplasmin substrate is N,N-dimethyl-p-phenylendiamine.

3. The method in claim 1 wherein the concentration of ceruloplasmin is determined by absorbance/ml enzyme method and standard curve method.

4. The method in claim 3 wherein the standard curve is prepared by serial dilutions of concentrated human ceruloplasmin and measuring the ceruloplasmin activity of said serial dilutions.

5. The method in claim 1 wherein the optical density for oxidase activity of ceruloplasmin can be measured by a spectrophotometer at 550-560 nm.

6. The method in claim 1 wherein the at least one urine sample is collected from weeks of proestrus, estrus, and weeks 1 through the week of baseline progestagen levels or parturition of the uteal phase/pregnancy.

7. The method in claim 1 wherein no change in the concentration of ceruloplasmin through out the estrous cycle means said test subject is pseudopregnant.

8. The method in claim 1 wherein the concentration of ceruloplasmin is elevated in term pregnancies and remains increased for approximately half of a secondary rise in progestagens.

9. The method in claim 1 wherein the concentration of ceruloplasmin is elevated in term pregnancies and remains increased in the secondary rise in progestagen.

10. The method in claim 9 wherein the concentration of ceruloplasmin is elevated in term pregnancies and remains increased ranging from 42-71% of the secondary rise in progestagen.

11. The method in claim 9 wherein deviations in the ceruloplasmin concentration patterns during the secondary luteal phase indicate a reduced chance of a term pregnancy.

12. The method in claim 1 wherein the concentration of ceruloplasmin is inconsistent during a secondary luteal phase in pregnancy loss.

13. The method of claim 1 wherein the mammalian test subject is a panda.

14. The method of claim 1 wherein the mammalian test subject is a polar bear.

15. The method of claim 1 wherein the mammalian test subject is a lynx.

16. A pregnancy enzymatic test kit for detecting ceruloplasmin level in a test sample of urine from a mammal to determine pregnancy or lack of pregnancy of mammals, said kit comprising:
   a. A ceruloplasmin standard to construct a standard curve of ceruloplasmin;
   b. Assay buffer concentrate; and
   c. A substrate specific to detect ceruloplasmin urine sample.

17. The kit of claim 16 also comprising at least one vessel for adding the testing urine samples and standard curve samples.

18. The kit of claim 16 further containing instructions for the performance of the pregnancy test.

* * * * *